US011867657B2

(12) United States Patent
Vijjapu et al.

(10) Patent No.: US 11,867,657 B2
(45) Date of Patent: Jan. 9, 2024

(54) INGAZNO (IGZO) BASED SYSTEM FOR GAS DETECTION AT ROOM TEMPERATURE

(71) Applicant: KING ABDULLAH UNIVERSITY OF SCIENCE AND TECHNOLOGY, Thuwal (SA)

(72) Inventors: Mani Teja Vijjapu, Thuwal (SA); Sandeep G. Surya, Thuwal (SA); Saravanan Yuvaraja, Thuwal (SA); Khaled Nabil Salama, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 57 days.

(21) Appl. No.: 17/767,191

(22) PCT Filed: Oct. 1, 2020

(86) PCT No.: PCT/IB2020/059220
§ 371 (c)(1),
(2) Date: Apr. 7, 2022

(87) PCT Pub. No.: WO2021/070021
PCT Pub. Date: Apr. 15, 2021

(65) Prior Publication Data
US 2022/0365022 A1 Nov. 17, 2022

Related U.S. Application Data

(60) Provisional application No. 62/913,341, filed on Oct. 10, 2019.

(51) Int. Cl.
*G01N 27/407* (2006.01)
*G01N 27/414* (2006.01)
*G01N 33/00* (2006.01)

(52) U.S. Cl.
CPC ..... *G01N 27/4075* (2013.01); *G01N 27/4141* (2013.01); *G01N 33/0037* (2013.01)

(58) Field of Classification Search
CPC .......... G01N 27/4071; G01N 27/4035; G01N 27/4065; G01N 33/0037; G01N 33/0039;
(Continued)

(56) References Cited

U.S. PATENT DOCUMENTS 8,222,041 B2 * 7/2012 Ren ...................... G01N 33/004
436/127
8,436,396 B2 * 5/2013 Shinohara ............... H01L 33/42
257/E33.012
(Continued)

FOREIGN PATENT DOCUMENTS

CN 110010710 A * 7/2019 ..... H01L 31/022408
TW 201405123 A * 2/2014

OTHER PUBLICATIONS

Hsiao-Wen Zan et al., "Amorphous indium-gallium-zinc-oxide visible-light phototransistor with a polymeric light absorption layer", Applied Physics Letters, vol. 97, Nov. 18, 2010. (Year: 2010).*
(Continued)

*Primary Examiner* — David A. Rogers
(74) *Attorney, Agent, or Firm* — PATENT PORTFOLIO BUILDERS PLLC

(57) ABSTRACT

A gas sensor includes a gate electrode; a dielectric layer covering one surface of the gate electrode; an indium (In) gallium (Ga) zinc (Zn) oxide (O) (IGZO) thin-film formed over the dielectric layer, and first and second metallic electrodes formed on a surface of the IGZO thin-film to act as source and drain, respectively. The IGZO thin-film has an In concentration of 11%+/−3%, Ga concentration of 11%+/−3%, Zn concentration of 7%+/−3%, and O concentration of 71%+/−3%, with a sum of the concentrations being 100%,
(Continued)

and the gas interacts with the IGZO thin-film and changes a current through the IGZO thin-film.

19 Claims, 34 Drawing Sheets

(58) Field of Classification Search
CPC ............. G01N 33/004; G01N 33/0042; G01N 33/0044; G01N 33/0031; G01N 27/4073; G01N 27/4074; G01N 27/4076
See application file for complete search history.

(56) References Cited

U.S. PATENT DOCUMENTS

| | | | |
|---|---|---|---|
| 9,006,796 B2* | 4/2015 | Occhipinti | G01N 27/4141 257/253 |
| 9,068,118 B2* | 6/2015 | Zhou | C09K 11/873 |
| 10,134,913 B2* | 11/2018 | Jin | H01L 27/127 |
| 10,634,641 B2* | 4/2020 | Wang | G01N 27/4067 |
| 10,734,495 B2* | 8/2020 | Sato | H01L 21/02219 |
| 10,768,137 B2* | 9/2020 | Jeong | G01N 33/004 |
| 11,257,985 B2* | 2/2022 | Hwang | G01N 33/0011 |
| 11,493,491 B2* | 11/2022 | Isobayashi | G01N 1/4005 |
| 2011/0045600 A1* | 2/2011 | Ren | G01N 33/004 422/83 |
| 2012/0096928 A1* | 4/2012 | Occhipinti | G01N 27/4141 73/31.06 |
| 2012/0313096 A1* | 12/2012 | Kim | G03F 7/0007 438/483 |
| 2016/0077047 A1* | 3/2016 | Khamis | G01N 27/4146 506/3 |
| 2016/0315200 A1* | 10/2016 | Jin | H01L 27/1225 |
| 2019/0165120 A1* | 5/2019 | Sato | H01L 21/28026 |
| 2019/0257784 A1* | 8/2019 | Jeong | G01N 27/4141 |
| 2020/0000078 A1* | 1/2020 | Aiki | G01N 27/221 |
| 2020/0080977 A1* | 3/2020 | Isobayashi | G01N 27/40 |
| 2020/0400604 A1* | 12/2020 | Jung | G01N 27/129 |
| 2021/0080440 A1* | 3/2021 | Sugizaki | G01N 1/44 |
| 2021/0278365 A1* | 9/2021 | Yamada | G01N 27/4146 |
| 2022/0365022 A1* | 11/2022 | Vijjapu | G01N 27/4141 |

OTHER PUBLICATIONS

Hsiao-Wen Zan et al., "Room-temperature-operated sensitive hybrid gas sensor based on amorphous indium gallium zinc oxide thin-film transistors", Applied Physics Letters, vol. 98, Jun. 22, 2011. (Year: 2011).*

Dae Jin Yang et al., "Amorphous InGaZnO4 films: Gas sensor response and stability", Sensors and Actuators B: Chemical, Jul. 1, 2012. (Year: 2012).*

Toru Yoshikawa et al., "Thermal Conductivity of Amorphous Indium-Gallium-Zinc Oxide Thin Films", Applied Physics Express, No. 6, Jan. 25, 2013 (Year: 2013).*

Kuen-Lin Chen et al., "Gas sensing properties of indium-gallium-zinc-oxide gas sensors in different light intensity", Analytical Chemistry Research, No. 4, Mar. 10, 2015. (Year: 2015).*

Narendra Kumar et al., "Low temperature annealed amorphous indium gallium zinc oxide (a-IGZO) as a pH sensitive layer for applications in field effect based sensors", AIP Publishing Advance, No. 5, 2015. (Year: 2015).*

Hideo Hosono, "How we made the IGZO transistor", Nature Electronics, vol. 1, Jul. 2018. (Year: 2018).*

Jingu Kang et al., "Nano Pt-decorated transparent solution-processed oxide semiconductor sensor with ppm detection capability", Royal Society of Chemistry Advances, No. 9, Feb. 20, 2019. (Year: 2019).*

Hongyu Tang et al., "Ultra-High Sensitive NO2 Gas Sensor Based on Tunable Polarity Transport in CVD-WS2/IGZO p-N Heterojunction", ACS Applied Materials and Interfaces, No. 11, Oct. 2, 2019. (Year: 2019).*

He Zhang et al., "Optimizing the Properties of InGaZnOx Thin Film Transistors by Adjusting the Adsorbed Degree of Cs+ Ions", Materials, vol. 12, Jul. 18, 2019. (Year: 2019).*

Mutsunori Uenuma et al., "Flexible TEG Using Amorphous InGaZnO Thin Film", Journal of Electronic Materials, vol. 48, No. 4, Dec. 13, 2018. (Year: 2018).*

Kazushige Takechi et al., "Sensor applications of InGaZnO thin-film transistors", Japanese Journal of Applied Physics, No. 58, May 31, 2019. (Year: 2019).*

ESPACENET Machine Translation of CN 110010710 A Which Originally Published On Jul. 12, 2019. (Year: 2019).*

Huanhuan Yan et al., "Influence of InGaZnO Films with Different Ratios on Refractive Index Sensing Characteristics of LPFG", Coatings, No. 10, Oct. 14, 2020. (Year: 2020).*

Casals, O., et al., "A Parts Per Billion (ppb) Sensor for NO2 with Microwatt (muW) Power Requirements Based on Micro Light Plates," ACS Sensors, Feb. 13, 2019, vol. 4, No. 4, pp. 822-826, ACS Publications.

Dey, A., "Semiconductor Metal Oxide Gas Sensors: A Review," Materials Science and Engineering B, Jan. 5, 2018, vol. 229, pp. 206-217, Elsevier B.V.

International Search Report in corresponding/related International Application No. PCT/IB2020/059220, dated Feb. 10, 2021.

Kang, Y., et al., "Intrinsic Nature of Visible-Light Absorption in Amorphous Semiconducting Oxides," APL Materials, Mar. 17, 2014, Article vol. 2, No. 3, 2014, pp. 032108-1-032108-7, AIP Publishing.

Kim, K. S., et al., "Toward Adequate Operation of Amorphous Oxide Thin-Film Transistors for Low-Concentration Gas Detection," ACS Applied Materials & Interfaces, Mar. 1, 2018, vol. 10, No. 12, pp. 10185-10193, ACS Publications.

Knobelspies, S., et al., "Photo-Induced Room-Temperature Gas Sensing with a-IGZO Based Thin-Film Transistors Fabricated on Flexible Plastic Foil," Sensors, Jan. 26, 2018, vol. 18, No. 358, pp. 1-10.

Nomura, K., et al., "Room-Temperature Fabrication of Transparent Flexible Thin-Film Transistors using Amorphous Oxide Semiconductors," Nature, Nov. 25, 2004, vol. 432, No. 7016, pp. 488-492, Nature Publishing Group.

Park, M.-J., et al., "Improvement of NO2 Gas-Sensing Properties in InGaZnO Thin-Film Transistors by a Pre-Biasing Measurement Method," Semiconductor Science and Technology, May 22, 2019, vol. 34, 065010, pp. 1-10, IOP Publishing Ltd.

Patil, N., "Photoelectrocatalytic Sensor for Volatile Organic Compounds using Indium Gallium Zinc Oxide Thin Film Transistor," Graduate Faculty of North Carolina Statement University, Dec. 31, 2010, pp. 1-113.

Vorobyeva, N., et al., "Highly Sensitive ZnO(Ga, In) for Sub-ppm Level NO2 Detection: Effect of Indium Content," Chemosensors, Jun. 1, 2017, vol. 5, No. 2, pp. 1-11.

Written Opinion of the International Searching Authority in corresponding/related International Application No. PCT/IB2020/059220, dated Feb. 10, 2021.

Yang, D.J., et al., "Amorphous InGaZnO4 Films: Gas Sensor Response and Stability," Sensors and Actuators B: Chemical, Jul. 1, 2012, vol. 171, pp. 1166-1171, Elsevier B.V.

* cited by examiner

INGAZNO (IGZO) BASED SYSTEM FOR GAS DETECTION AT ROOM TEMPERATURE

CROSS-REFERENCE TO RELATED APPLICATIONS

This application is a U.S. National Stage Application of International Application No. PCT/162020/059220, filed on Oct. 1, 2020, which claims priority to U.S. Provisional Patent Application No. 62/913,341, filed on Oct. 10, 2019, entitled "INTEGRATED THIN FILM ELECTRONIC BASED MICROSYSTEM FOR TOXIC GAS DETECTION AT ROOM TEMPERATURE," the disclosures of which are incorporated herein by reference in their entirety.

BACKGROUND

Technical Field

Embodiments of the subject matter disclosed herein generally relate to a sensor and associated system for gas detection based on a thin-film transistor, and more particularly, to a gas sensor that uses a IGZO thin-film as an active layer for sensing $NO_2$ at room temperature and has a quick recovery time without using a high temperature or continuous light exposure.

Discussion of the Background

It is known that the air quality has a serious influence on the human health, but the worldwide rapid industrialization and urbanization have resulted in increased pollution, especially due to the automobile and industry emissions of various toxic gases. Automobile emissions are one of the major sources of pollution, among which nitrogen oxides ($NO_x$) are the major constituents of concern as they lead to particulate matter ($PM_{2.5}$) production. Thus, there is a high demand for cost-effective air quality monitoring stations that use low-cost gas sensors, to be implemented at various locations, to monitor the amount of these gases.

The need for an accurate and economical way of sensing toxic gases has triggered interest in exploring inexpensive, highly sensitive, selective gas sensors. Among all these gases, as per Occupational Safety and Health Administration (OSHA) limits, $NO_2$ has a short time exposure limit (STEL) as 1 ppm, which means the exposure limit of 1 ppm $NO_2$ is 15 minutes. Changes in the pulmonary functions in healthy patients have been found for 2-3 ppm exposure to $NO_2$. An exposure of 4 hours to 90 ppm $NO_2$ is estimated to be the lethal concentration ($LC_{50}$), and exceeding this limit has adverse effects on human respiratory systems, such as causing asthma and chronic pulmonary diseases. Hence, detection of the $NO_2$ presence with higher sensitivity, selectivity, and lower detection limit is vital for human health and safety.

Conventional gas sensing technologies include electrochemical, metal oxide semiconductor (MOS), optical, acoustic, chromatography, and calorimetric technologies. In particular, the MOS gas sensors are shown to fulfil most of the criteria for gas sensing applications. Many efforts are being made to enhance the sensitivity and selectivity of these sensors by exploring metal oxide nanoparticles, nanocomposites, nano-structures, and metal-organic frameworks, thereby increasing the surface to volume ratio and number of reactive sites to the enhance gas diffusion. Although many gas and vapor sensors based on nanomaterials have been reported, implementing them in an actual system for real-time applications is still a challenge because of mass production and reproducibility issues.

Complementary MOS (CMOS) compatible sensors that can be easily integrated with CMOS circuitry have considerable potential in realizing gas sensing systems. However, the existing MOS gas sensors are power-hungry since they are active either at high temperatures (>200° C.) [1] or under continuous light activation. Furthermore, high-temperature MOS sensors cannot be used in some critical environments, for example, an enclosure where flammable or explosive gas materials may be present as these materials have ignition temperatures in the range of the operating temperatures of these sensors. In this regard, if the medium in which the sensor operates includes $H_2S$, which has an ignition point of 260° C., there is a danger to use the sensor. Light-activated MOS devices are a better choice in such cases, but their sensitivity is very low when compared to thermally activated devices because of the limited optical response.

Recently, for low concentration $NO_2$ detection, a zinc oxide nanoparticle based light active electrochemical sensor has been reported, but it must be turned on all the time to keep the sensing layer active [2], making it power-hungry. Hence, developing an MOS sensor that is active at room temperature and without continuous light activation is desired.

A thin-film transistor (TFT) utilizing indium gallium zinc oxide (IGZO) was reported [3] and this device has promising properties, such as high carrier mobility and high carrier concentration, making it the best semiconducting channel candidate for the TFTs. However, non-passivated IGZO TFTs' electrical characteristics are sensitive to the ambient oxygen. Although there are reports that describe the use of the IGZO as an active layer to detect $NO_2$ [3-6], these sensors require either UV activation [5] or the presence of a high temperature for sensing and recovery [3, 4, 6], which are typical requirements of the MOS gas sensors.

In this regard, [4] discloses a TFT device that uses an amorphous InGaZnO material as a channel and sensing layer for $NO_2$ gas detection. However, the authors of this paper indicate (see, for example, page 10191, right hand side column) that "the lack of recovery behavior by a high gate bias reveals that the $NO_2$ gas is likely to form strong chemical bonds, rather than simply absorbing on the amorphous IGZO. These results implicitly indicate that such a sensing reaction makes recovery more difficult and that the supply of additional external energy may be needed. Although conventional resistor-type oxide gas sensors are known to require relatively high temperatures for fast recovery, our a-IGZO TFT sensors are expected to be processed at relatively low temperatures of 100° C. because the $NO_2$ actively reacts with the limited surface of the active layers."

This disclosure in [4] clearly indicates that there is a problem with the existing IGZO TFT sensors in the sense that the recovery time is long and it requires a higher temperature than the room temperature for a correct operation, i.e., 100° C. for this device, which is quite taxing on the power supply of such a sensor.

A similar sensor is presented in [5] and this reference indicates on page 6 that "To analyze the dependence between gas concentration and sensor signal, the $I_D$ response is fitted with the exponential function $$I(t) = A \cdot \exp^{\left(-\frac{t}{\varphi}\right)} + c.$$

The fits show an average $R^2$-value of 0.9973±0.0013. The extracted time constants τ for adsorption and desorption of $NO_2$ are $\tau_{adsorption}$=13.5±3.6 min $T_{desorption}$=50.2±2.9 min." This sensor shows the same problem as the sensor in [4], i.e., the recovery time is so long (50 minutes for this case) that the sensor becomes impractical. In this regard, it is noted that a recovery time of 50 minutes means that the sensor cannot measure the presence of $NO_2$ for that time. The article recognizes this problem by stating, on the same page, that "It is worth mentioning that the sensor response is quite slow . . . . " The solution proposed by this reference is to add a buried microheater structure to recover the sensor quicker, which would lead to energy consumption, which is not desired for a small, autonomous sensor.

Thus, there is a need for a new TFT IGZO based sensor that is very sensitive to $NO_2$ gases, but at the same time is capable of a quick recovery time without using a high temperature or a continuous light exposure.

BRIEF SUMMARY OF THE INVENTION

According to an embodiment, there is a gas sensor that includes a gate electrode, a dielectric layer covering one surface of the gate electrode, an indium (In) gallium (Ga) zinc (Zn) oxide (O) (IGZO) thin-film formed over the dielectric layer, and first and second metallic electrodes formed on a surface of the IGZO thin-film to act as source and drain, respectively. The IGZO thin-film has an In concentration of 11%+/−3%, Ga concentration of 11%+/−3%, Zn concentration of 7%+/−3%, and O concentration of 71%+/−3%, with a sum of the concentrations being 100%, and the gas interacts with the IGZO thin-film and changes a current through the IGZO thin-film.

In another embodiment, there is a gas detection system for determining a concentration of a gas. The system includes a first transistor having an indium (In) gallium (Ga) zinc (Zn) oxide (O) (IGZO) thin-film formed over a dielectric layer, wherein the IGZO thin-film interacts with the gas and changes a sensing current through the first transistor, a second transistor (T1) electrically connected to the first transistor to form a master branch, wherein the second transistor (T1) has an identical structure as the first transistor, and a corresponding IGZO thin-film is encapsulated with a material to prevent an interaction between the IGZO thin-film of the second transistor (T1) and the gas, while the IGZO thin-film of the first transistor is free to directly interact with the gas, third and fourth transistors (T2, T3) electrically connected to each other and forming a secondary branch, wherein the third and fourth transistors (T2, T3) are identical to the second transistor (T1), and an inverter electrically connected to the third and fourth transistors (T2, T3). The inverter receives a voltage due to (1) a reference current from the third transistor (T2), and (2) a current from the fourth transistor (T3), which is identical to the sensing current of the first transistor, and outputs a digital value indicative of the concentration of the gas.

In still another embodiment, there is a gas detection system for determining a concentration of a gas, and the system includes a first transistor having a gate electrically connected to a drain, a second transistor (T1) having a gate connected to a variable power source, and an inverter connected to a source of the first transistor and to a drain of the second transistor (T1). The first transistor includes an indium (In) gallium (Ga) zinc (Zn) oxide (O) (IGZO) thin-film, which is exposed to an ambient, the second transistor includes a corresponding IGZO thin-film, which is encapsulated to not be exposed to the ambient, and for each applied voltage $V_{GS}$ at the gate of the second transistor T1, the inverter receives a voltage due to a sensing current generated by the first transistor and a reference current generated by the second transistor, and generates a digital value indicative of the concentration of the gas.

According to yet another embodiment, there is a method for measuring a gas concentration, and the method includes exposing a first transistor having an indium (In) gallium (Ga) zinc (Zn) oxide (O) (IGZO) thin-film to a gas while at room temperature; generating a sensing current through the first transistor as the IGZO thin-film directly interacts with the gas; generating a reference current with a second transistor (T1), wherein the second transistor (T1) is identical to the first transistor, except that a corresponding IGZO thin-film of the second transistor (T1) is fully encapsulated to prevent an interaction with the gas; supplying the sensing current and the reference current to an input of the inverter; outputting a digital value at an output of the inverter that is indicative of the gas concentration; and recovering the first transistor by illuminating the IGZO thin-film with blue light at room temperature.

BRIEF DESCRIPTION OF THE DRAWINGS

Fora more complete understanding of the present invention, reference is now made to the following descriptions taken in conjunction with the accompanying drawings, in which:

FIGS. 8A and 8B illustrate various characteristics of the IGZO TFT gas sensor while

FIG. 13A illustrates a common source configuration of a IGZO based transistor while

DETAILED DESCRIPTION OF THE INVENTION

The following description of the embodiments refers to the accompanying drawings. The same reference numbers in different drawings identify the same or similar elements. The following detailed description does not limit the invention. Instead, the scope of the invention is defined by the appended claims. The following embodiments are discussed, for simplicity, with regard to a TFT IGZO based sensor that detects $NO_2$. However, the embodiments to be discussed next are not limited to a $NO_2$ sensor, but may be applied to sensors that detect other gases or liquids.

Reference throughout the specification to "one embodiment" or "an embodiment" means that a particular feature, structure or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments.

According to an embodiment, a CMOS compatible gas sensor using IGZO as the active layer for sensing $NO_2$ at room temperature, without continuous light activation, is discussed. The gas sensor is configured to recover after exposure to the gas through light illumination, which is a more power-efficient solution than existing MOS gas sensors, because it does not require a high temperature or continuous light activation for sensing. State of the art gas sensing systems are expensive, power-hungry, and bulky, impeding their large scale deployment for air quality monitoring stations. Thin-film electronic microsystems discussed herein use a passivated IGZO channel n-type TFT and a non-passivated channel TFT as the $NO_2$ gas sensor. One of these microsystems yields a 5-bit digital output corresponding to the $NO_2$ concentration without any additional hardware for readout/amplifying and analog to digital conversion (ADC). Other microsystems are also presented.

Figure 1:
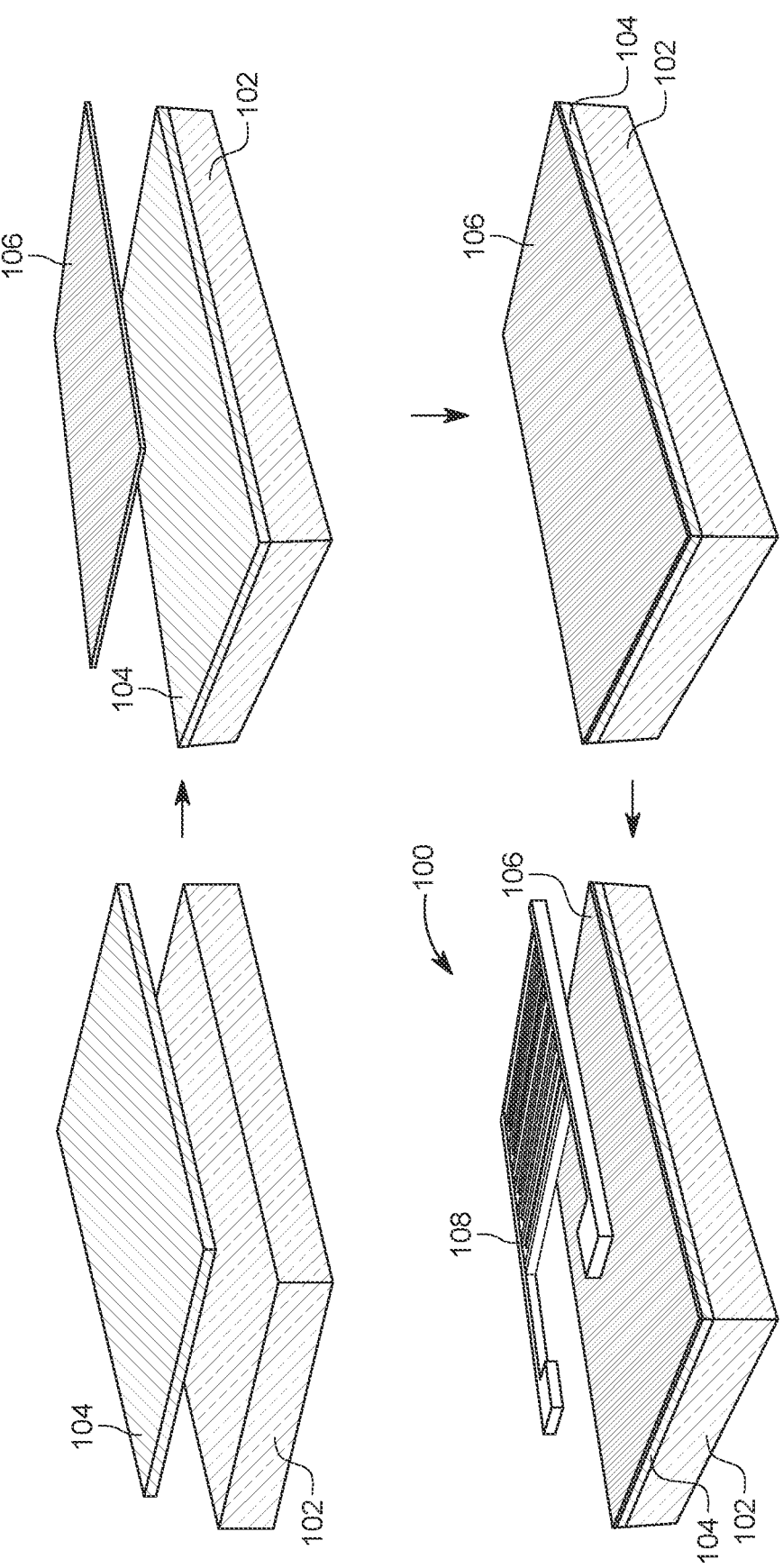
FIG. 1 is a schematic diagram of a process for making an IGZO thin-film based sensor.

According to an embodiment, a bottom gate, top contact, IGZO TFT based gas sensor is fabricated so that the IGZO material serves the dual role of a channel layer for the transistor and also as a sensing layer to detect the $NO_2$ gas. As previously discussed, this device may detect other gases, but for simplicity, only the $NO_2$ gas is discussed herein. A bottom to top approach for fabricating the IGZO TFT is shown in FIG. 1. More specifically, an n-type doped silicon (Si) wafer 102 with (100) orientation is used to serve as the bottom gate electrode. Then, the Si wafer is thoroughly cleaned to remove the organic and metal impurities by dipping in, for example, a Piranaha solution, for 5 minutes, and to remove native oxides by dipping it in buffered oxide etch solution for 5 minutes. Subsequently, a layer 104 of silicon oxide ($SiO_2$) having a thickness of 150 nm (other values may be used) was deposited through thermal oxidation in a thermal furnace to serve as the gate oxide (dielectric film) for the IGZO TFT 100. In the following, as the transistor 100 is also used to detect the concentration of the gas, the term "transistor" is used interchangeably with the term "sensor." An IGZO thin-film 106 (e.g., having a thickness of about 10 nm, but other thickness between 5 and 60 nm may be used) is deposited by RF sputtering (other methods may be used) using an IGZO target ($In_2O_3$—$Ga_2O_3$—ZnO 1:1:2 mol %). The sputtering may be performed at 60 W RF Power in the presence of Argon/Oxygen (20 SCCM/3 SCCM) plasma at 5 mtorr deposition pressure. A rapid thermal processing (RTP) may be applied to the device, to improve the TFT device stability, and the RTP may be performed at 500° C. for 4 minutes in the oxygen ambience. Interdigitated top electrodes made of titanium (Ti)/gold (Au) 108 are then deposited on the IGZO thin-film 106, using a lift-off process, which is followed by a photo-lithography process to pattern the interdigitated electrodes. The metal deposition is performed with a DC magnetron sputtering at 400 W in the presence of Ar plasma to yield 10 nm and 100 nm thickness of Ti and Au respectively. Other thicknesses for the electrodes may be used and also other processes for making the electrodes may be used, for example, thermal evaporation.

Figure 2:
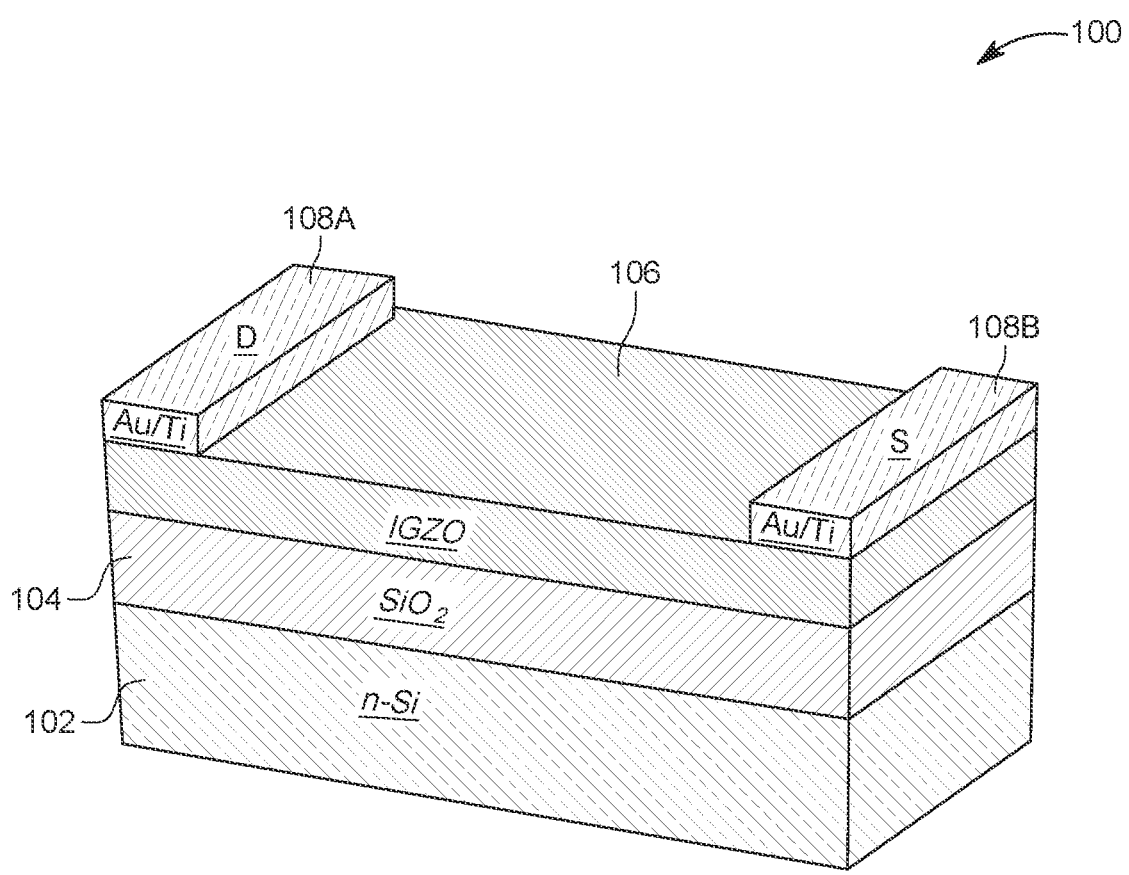
FIG. 2 is an overall view of the IGZO thin-film based sensor for measuring a gas concentration.

A schematic illustration of the sensor 100 is shown in FIG. 2. The IGZO thin-film 106 is very smooth, with a mean roughness of 0.23 nm. To overcome the problems of the IGZO based sensors discussed in the Background section, the inventors have discovered that the concentrations of the In, Ga, Zn and O elements in the IGZO thin-film 106 influence the recovery of the thin-film after interacting with the $NO_2$ gas. More specifically, the inventors have observed that by selecting the In concentration to be in a certain range, makes the IGZO thin-film to quickly recover by removing the $NO_2$ gas after it interacts with the IGZO thin-film 106, with the help of a low electrical field that is generated as discussed later. In addition, by selecting the concentration of the elements of the IGZO thin-film to be within certain ranges, which are discussed next, the time required to desorb the nitrogen from the active layer decreases dramatically when compared to the existing devices, so that there is no need for a continuous illumination of the active layer for the recovery process.

Figure 3:
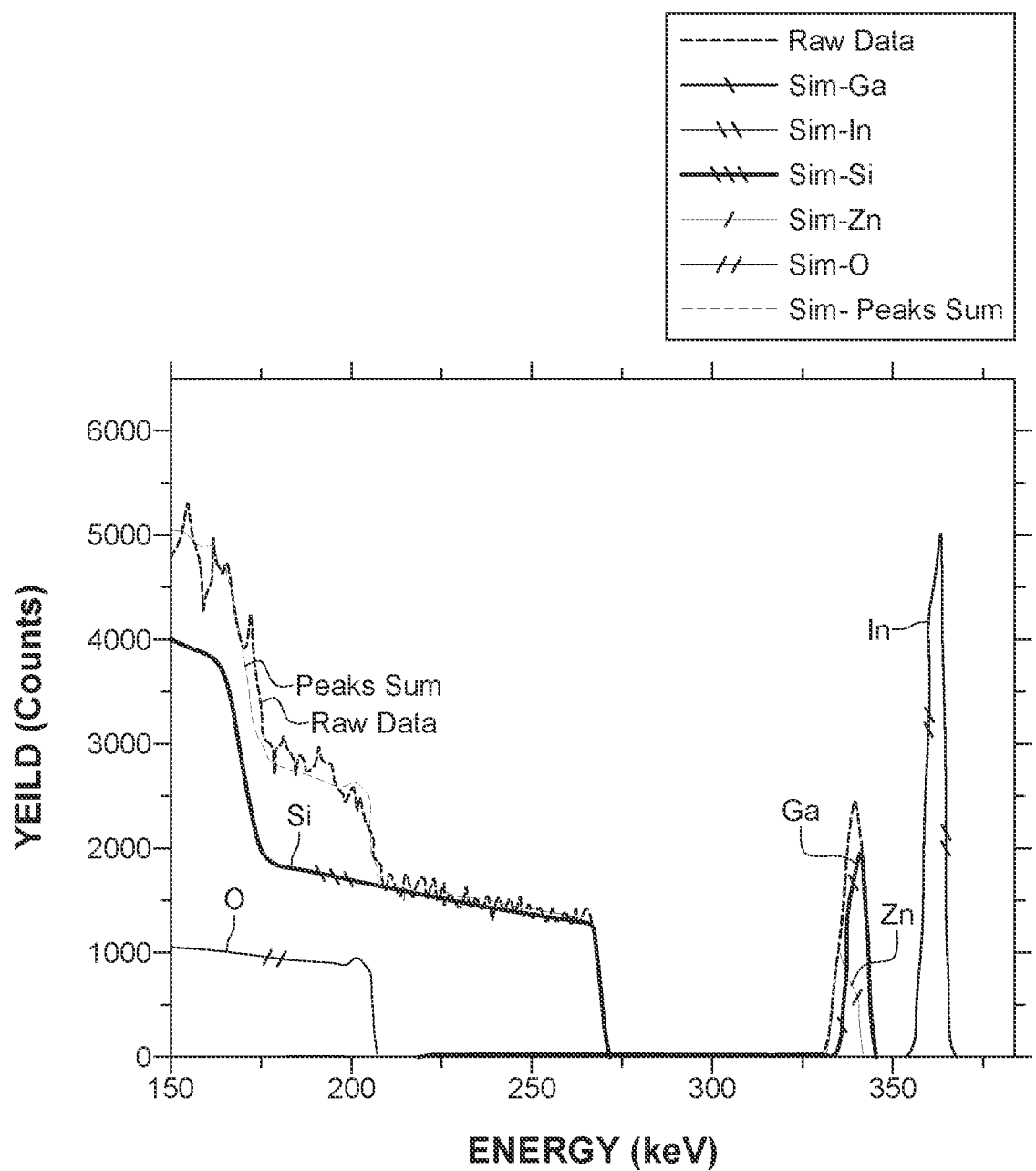
FIG. 3 illustrates a high-resolution Rutherford backscattering spectroscopy analysis of the IGZO thin-film.

The individual concentrations of the elements making up the active layer 106 of the sensor 100 were analyzed with a high-resolution Rutherford backscattering spectroscopy (RBS) and FIG. 3 illustrates the results for each element of the IGZO thin-film 106. For the embodiment illustrated in FIG. 2, the concentration of the In is 11.28%, the concentration of the Ga is 10.74%, the concentration of the Zn is 6.80%, and the concentration of the O is 71.17% in terms of weight. The inventors have observed that if any one or more of these concentrations deviate by not more than 10% from the values listed above, the advantageous properties of the IGZO thin-film 106 discussed herein still hold. In other words, in one embodiment, the In concentration is 11%, the Ga concentration is 11%, the Zn concentration is 7% and the O concentration is 71%. However, in another embodiment, the In concentration is 11%+/−3%, the Ga concentration is 11%+/−3%, the Zn concentration is 7%+/−3% and the O concentration is 71%+/−3% with a total sum of the concentrations being 100%. To describe these variations in the concentrations of the individual elements for which the recovery of the IGZO layer 106 are maintained, in the following, the term "substantially" is used to refer to these concentrations, and this term means that the value to which it refers can vary by +/−5%. In other words, an In concentration of substantially 11% means that it can be between 11+5% and 11−5%. In one application, no other materials are part of the IGZO thin-film except those listed above.

Figure 4:
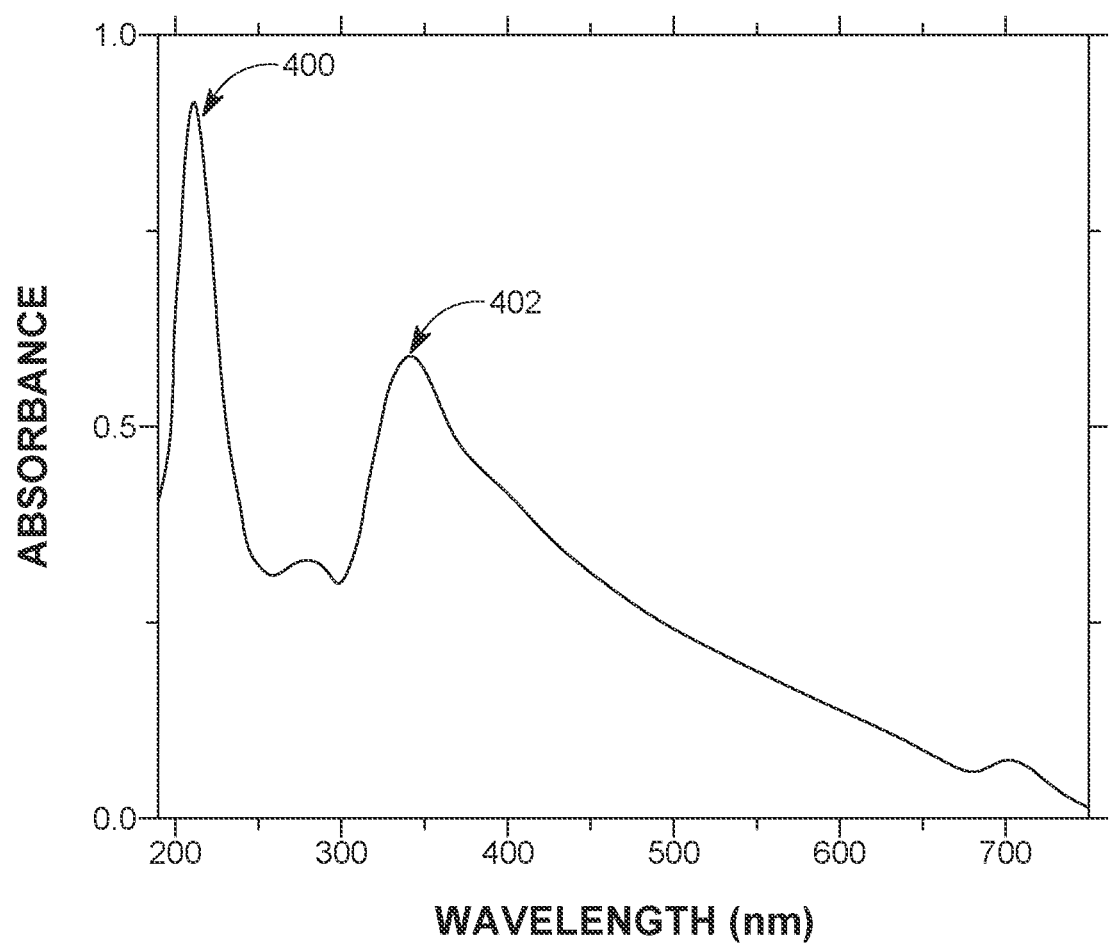
FIG. 4 illustrates the absorbance of the IGZO thin-film.

The sensor 100 having the elements In, Ga, Zn and O with substantially the concentrations noted above shows good absorbance in the UV and blue wavelength regime, as illustrated in FIG. 4. In this regard, note that the sensor 100 has a first peak light absorbance 400 at about 220 nm and a second peak light absorbance 402 at about 350 nm. In one implementation, the rapid thermal processing is performed on the sensor to improve the TFT device stability.

Figure 5A:
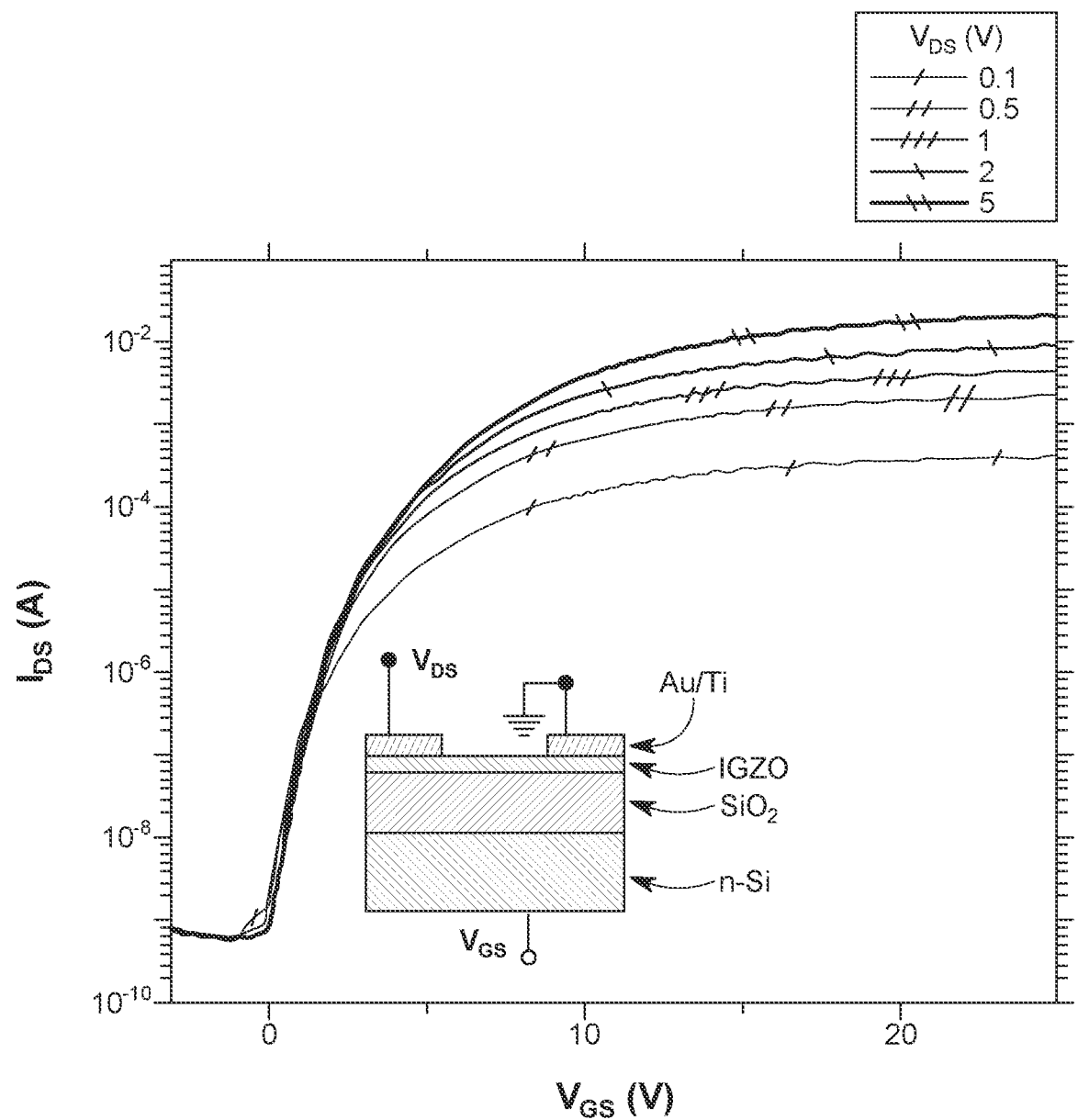
FIG. 5A illustrates the transfer characteristics and FIG. 5B illustrates the output characteristics of an IGZO thin-film-transistor (TFT)
Figure 5B:
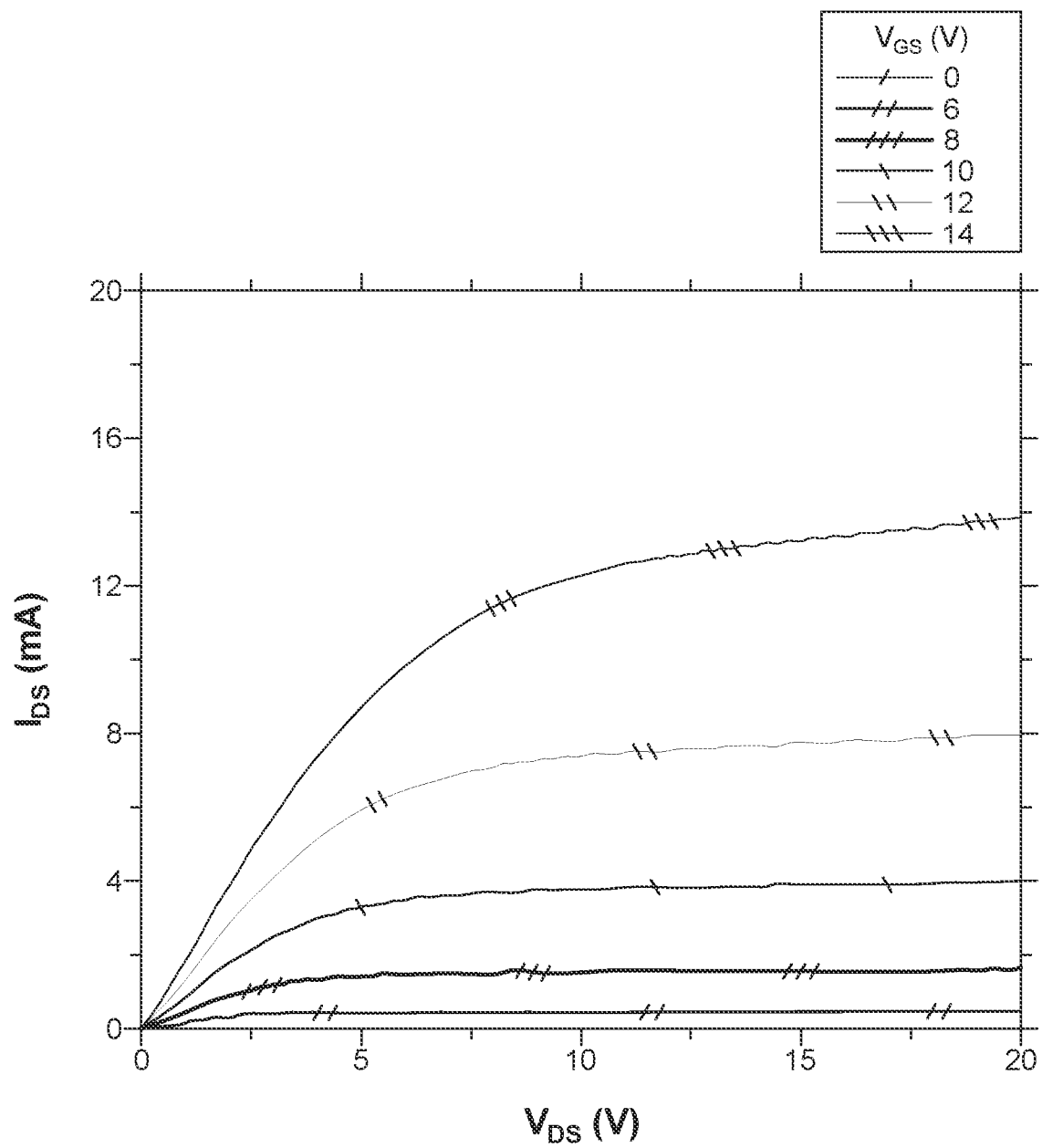
Figure 6A:
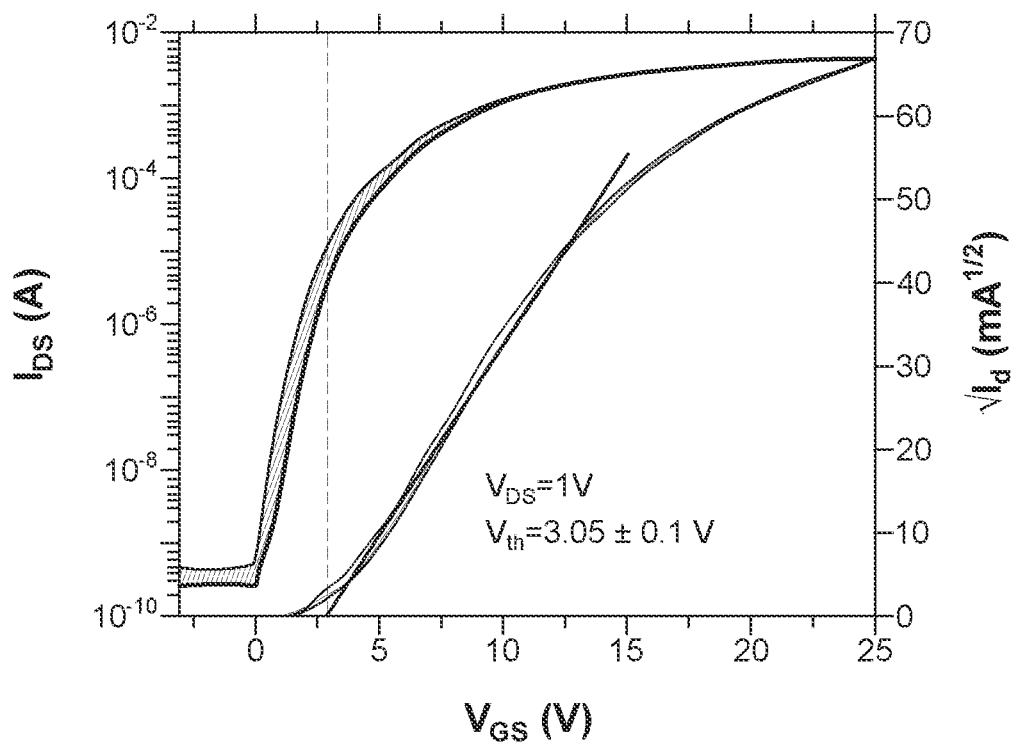
FIG. 6A shows the repeatable transfer characteristics and FIG. 6B shows the repeatable output characteristics at constant bias of the IGZO TFT at room temperature.
Figure 6B:
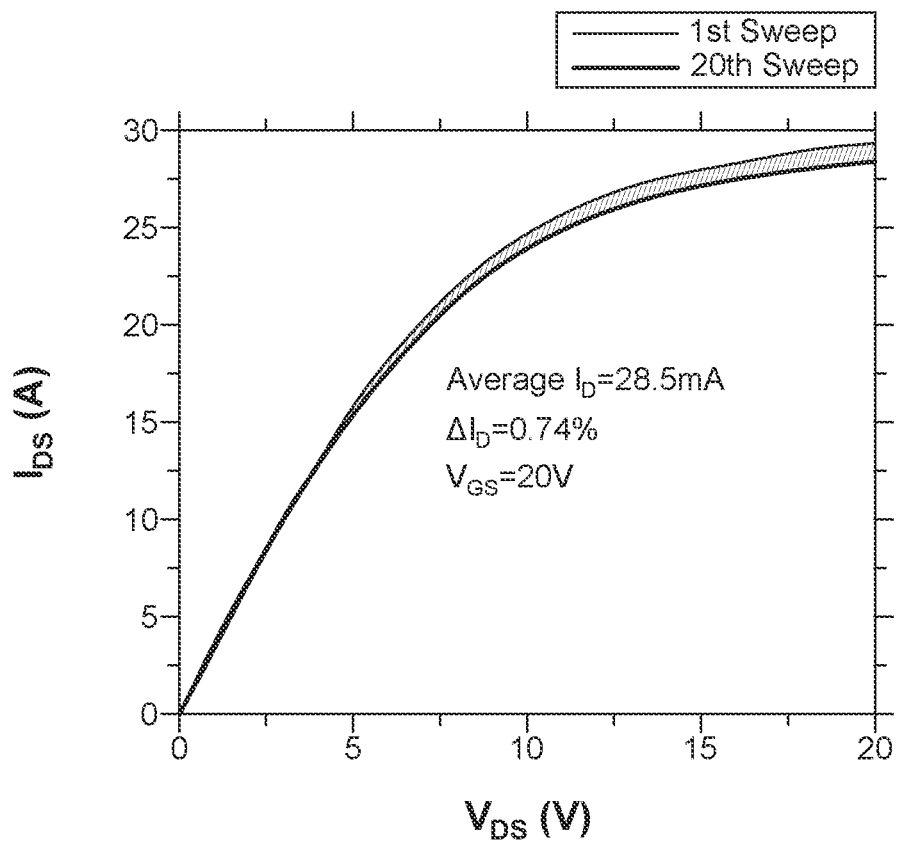

The IGZO TFT 100 was characterized using a semiconductor parameter analyzer. The sensor 100 shows an ON/OFF ratio of ~$10^7$, high linear mobility (0.23 $Cm^2V^{-1}s^{-1}$), low subthreshold swing (0.49 V $dec^{-1}$), and stable electrical characteristics. The transfer and output characteristics of the fabricated sensor 100, at various bias voltages, are presented in FIGS. 5A and 5B, respectively. Existing IGZO TFTs were reported to possess instabilities due to the traps within the channel layer, resulting in a threshold voltage ($V_{th}$) shift due to the bias stress. This can be minimized through fabrication process strategies. The sensor 100 was optimized to have minimal instabilities through the RTP process, and the stability of the sensor is shown in FIGS. 6A and 6B. These figures show the repeatable transfer and repeatable output at constant bias, at room temperature.

Figure 7:
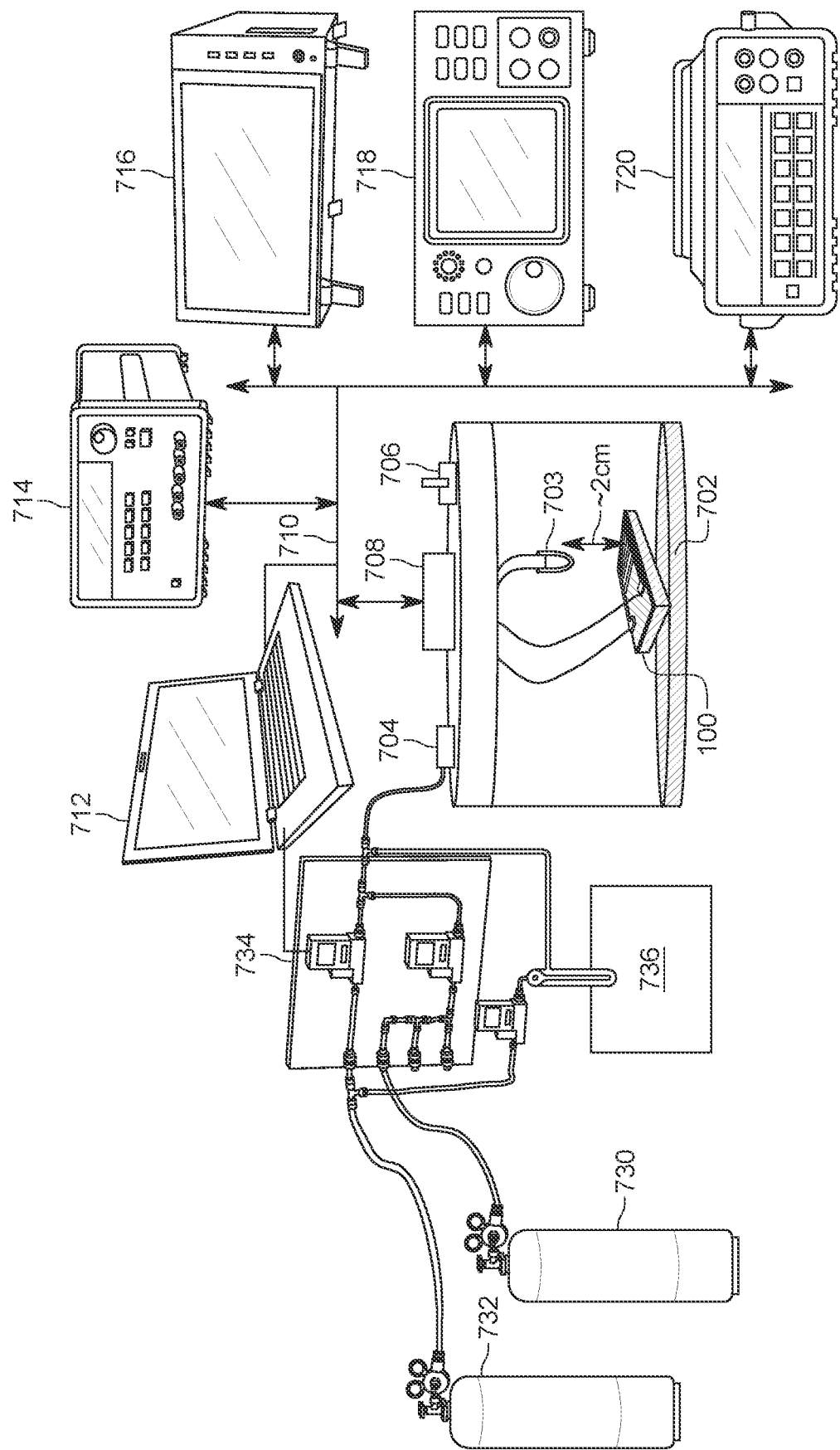
FIG. 7 shows a test setup for measuring various properties of the IGZO TFT gas sensor.

Multiple IGZO TFTs 100 were tested to characterize their gas response, for various toxic gases in a tailor-made gas configured system 700 as shown in FIG. 7. The system 700 includes a test chamber 702 having a gas inlet 704 through which any desired gas is introduced into the test chamber. The sensor 100 was placed inside the test chamber 702. The test chamber also has a gas exhaust 706, which is used to remove the studied gas. An electrical interface 708 of the test chamber is connected to a light source 703 and to a communication network 710, which is also connected to a computing system 712, a voltage source 714, a semiconductor parameter analyzer 716, an oscilloscope 718, and a multimeter 720. One or more of these instruments communicate with the interface 708, and can apply a desired voltage, current, power or other parameters to the sensor 100. The interface 708 may also be used to measure various characteristics of the sensor 100 and also to introduce add-ons such as light source 703.

A source light 703 is also placed inside the test chamber 702, for illuminating the sensor 100, as discussed later, to recover the active layer 106 after interacting with the studied gas. The source light 703 may be an LED, having a desired wavelength. The source light 703 may be controlled from the computing system 712, through the communication network 710 and interface 708. The system 700 further includes various gas containers 730, 732, for generating a desired gas to be tested in the test chamber. A mass flow controller 734, which is controlled by the computing device 712, may control the flow of the desired gas having the desired concentration.

Figure 8A:
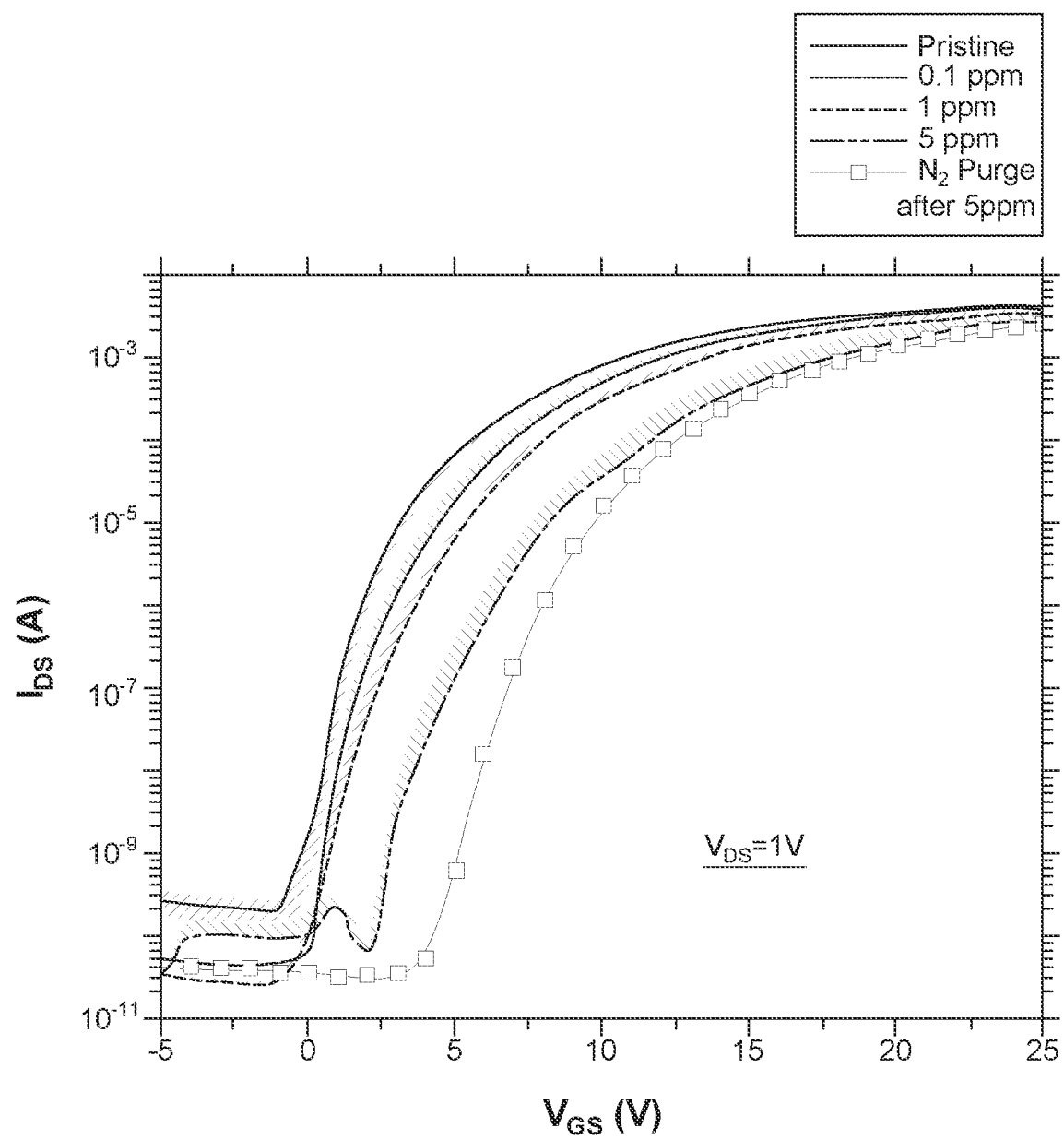
Figure 8B:
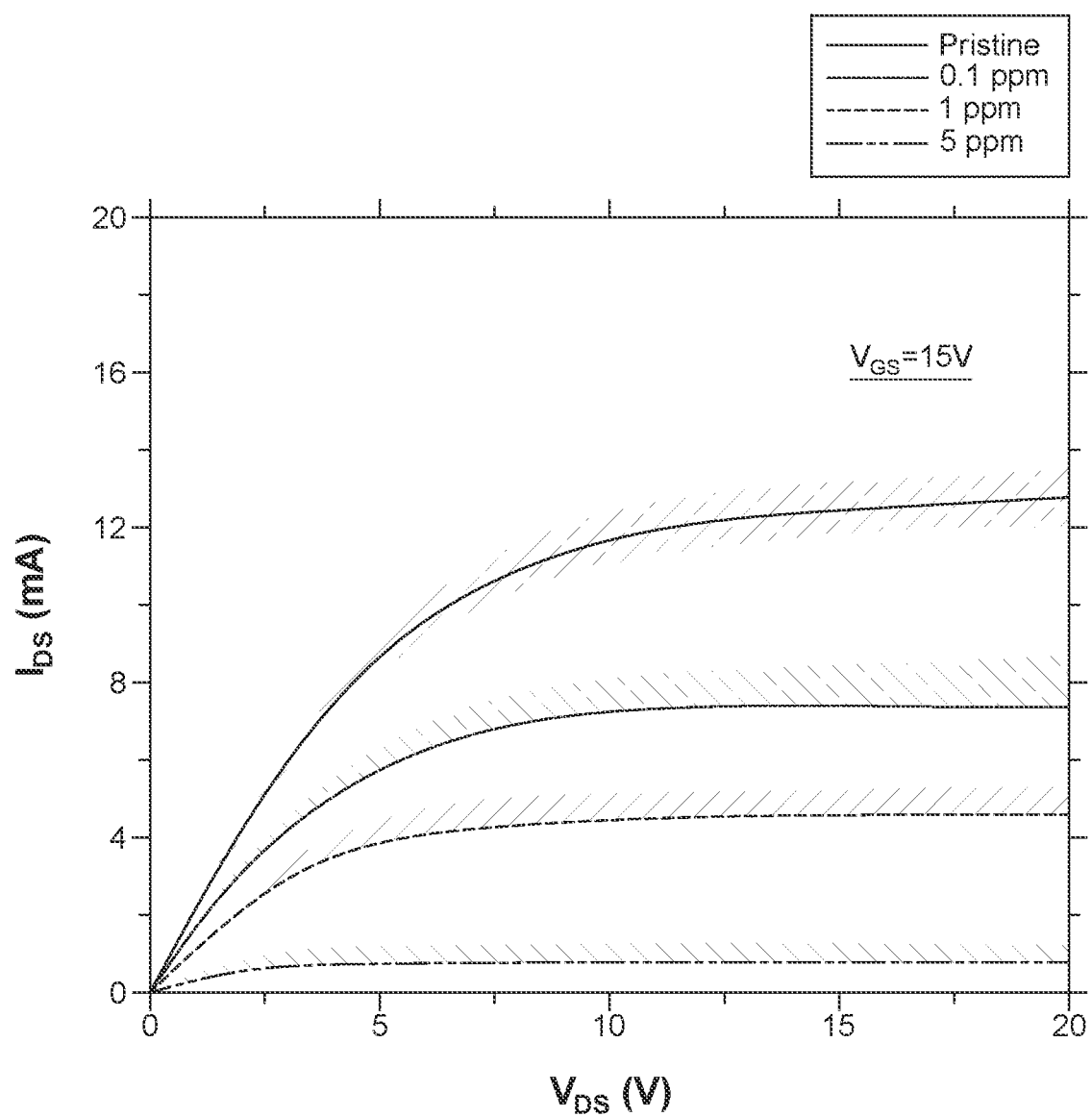

The concentrations of the various gases supplied to the test chamber 702 for testing the sensor 100 were controlled by diluting them with nitrogen ($N_2$), from the gas container 732. The $N_2$ gas was used as the carrier gas. The $N_2$ gas was also used during the recovery of the active layer 106. The inventors have found that the semiconducting properties of the IGZO based sensor 100 are susceptible to the $NO_2$ adsorption at room temperature, as illustrated in FIGS. 8A to 8B. For this investigation, the transfer (FIG. 8A) and output characteristics (FIG. 8B) of the IGZO TFTs were monitored every minute after exposing the sensor 100 to various concentrations (100 ppb to 5 ppm) of the $NO_2$ gas at room temperature. The transfer characteristics and output characteristics were measured by keeping $V_{DS}$=1 V and $V_{GS}$=15 V, respectively. It was observed that with the increase in the $NO_2$ gas concentration, there was a positive shift in the $V_{th}$ and a decrease in the drain current ($I_D$) of the TFT. These findings are consistent with the reported IGZO TFT based sensors [4, 6], as shown in FIGS. 8A and 8B.

Figure 8C:
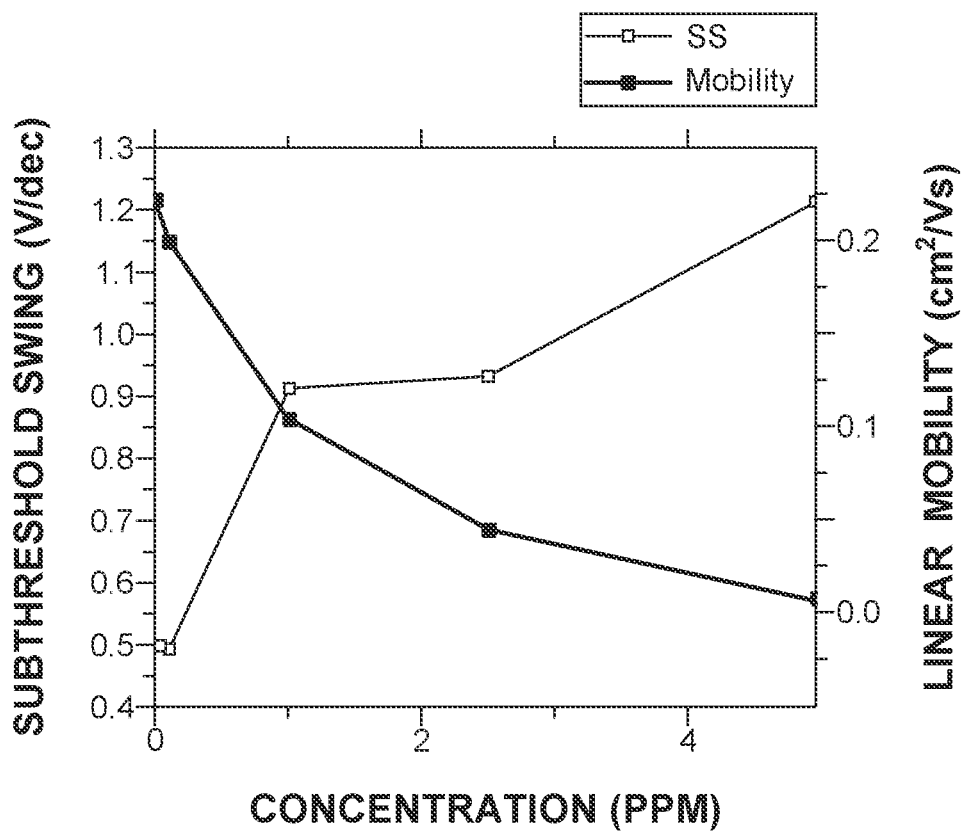
FIGS. 8C to 8F illustrate the sensitivity of the various characteristics of the IGZO TFT gas sensor to various concentrations of the measured gas.
Figure 8D:
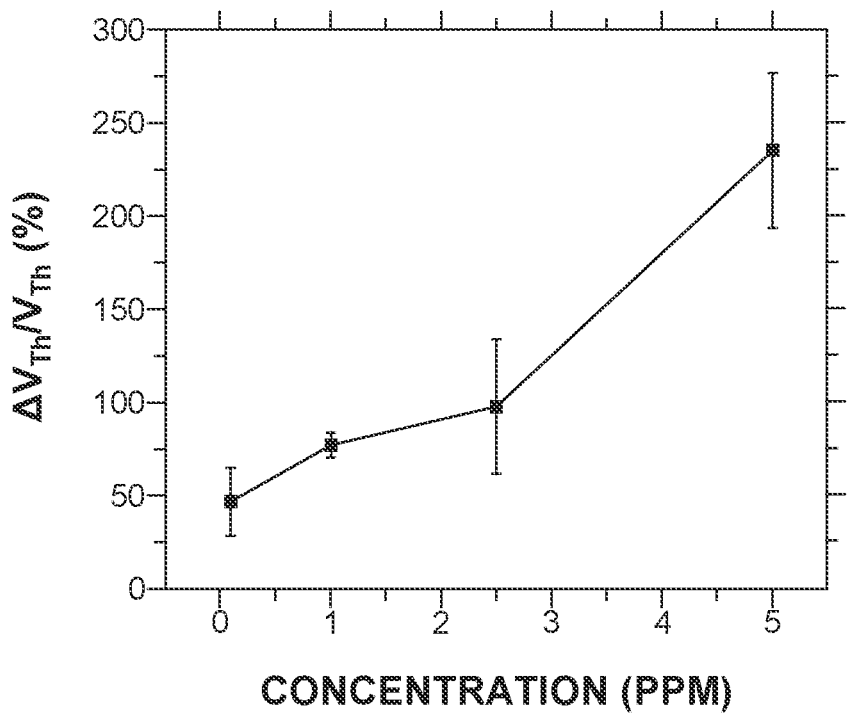
Figure 8E:
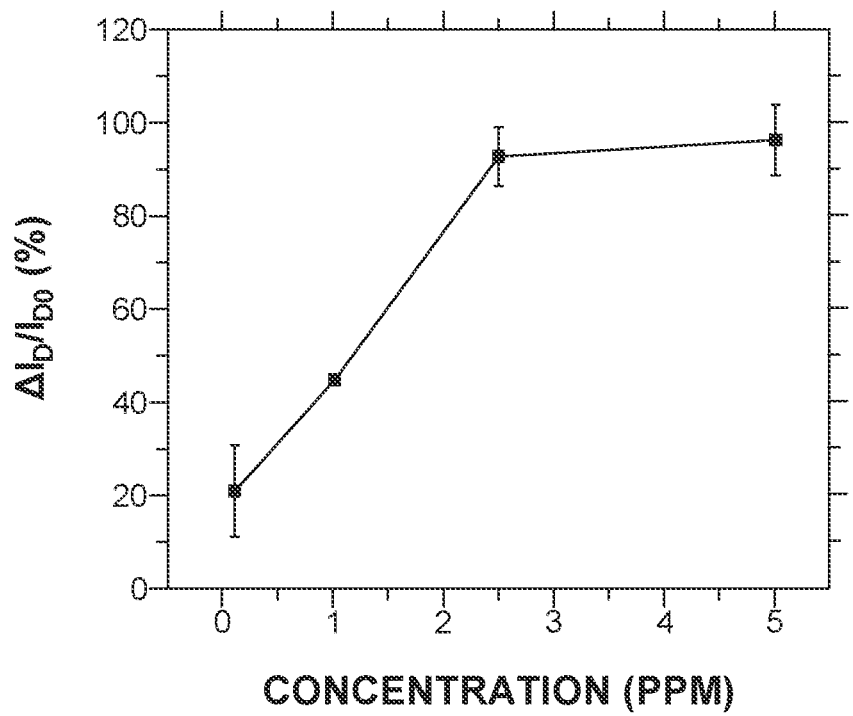
Figure 8F:
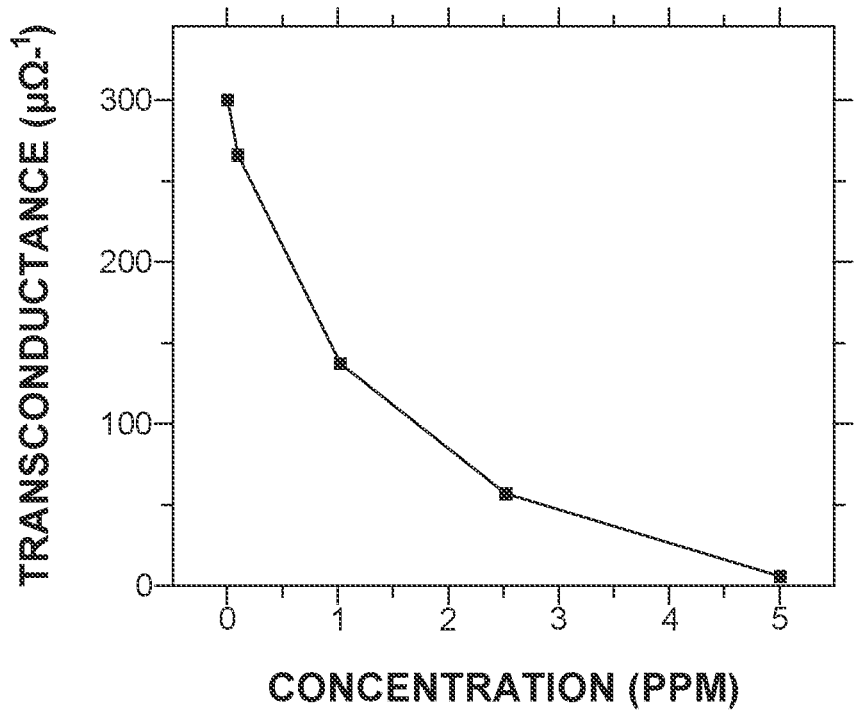

There was a substantial change in the $V_{th}$ and $I_D$ of IGZO TFTs, which is proportional to the concentration of the $NO_2$ gas, as illustrated in FIGS. 8D and 8E, respectively. Thus, any of these two parameters may be measured for estimating the concentration of the measured gas. The IGZO TFT parameters, such as linear field-effect mobility, subthreshold swing, and transconductance in the presence of the $NO_2$ gas, were extracted from transfer characteristics. It was observed that with the increase in the $NO_2$ concentration, the transconductance (see FIG. 8F) and the linear field-effect mobility (see FIG. 8C), which determine the conductivity and electronic transport of carriers in the channel, were proportionally reduced. The subthreshold swing (which describes the steepness of the $I_D$ transition from the OFF state to the ON state) increased with the rising $NO_2$ concentration as shown in FIG. 8C. The variation in these parameters indicates that there was adequate depletion of the charge carriers from the IGZO channel 106's surface due to the interaction with the $NO_2$ gas, as described by equation (1) below.

The $NO_2$ gas is a strong oxidizing agent and thus, the surface carriers of the IGZO channel 106 are involved in the reduction of the $NO_2$ gas molecules, as described by equation:

$$NO_2(gas)+e^-(IGZO\ surface) \rightarrow NO_2^-(ads). \tag{1}$$

The response of the threshold voltage $V_{th}$ and the drain current $I_D$ are given by the following equations:

$$\text{Response}(\%)(V_{th}) = \frac{V_{th\ after\ exposure} - V_{th\ pristine\ device}}{V_{th\ pristine\ device}} \cdot 100, \tag{2}$$

$$\text{Response}(\%)(I_D) = \frac{I_{D\ after\ exposure} - I_{D\ pristine\ device}}{I_{D\ pristine\ device}} \cdot 100. \tag{3}$$

From the transfer and output characteristics of the IGZO TFT and as shown in FIGS. 8D and 8E, the response (%) in terms of $V_{th}$ and $I_D$ was measured using the formula given by equation (2) and equation (3), respectively. The $V_{th}$ was extracted from the linear extrapolation of the $\sqrt{I_{DS}}$-$V_{GS}$ curve. The variation in the $I_D$ was maximum in the saturation region; hence, the sensors 100 were operated in saturation to assess the sensing performance.

For a gas or chemical sensor, a fast recovery of the device is desired because during the recovery period, the sensor cannot be used, and thus, potentially important information is missed. Because the channel 106 of the TFT 100 was oxidized after $NO_2$ exposure, these sensors cannot be recovered, unless external energy is provided, even after a prolonged $N_2$ purge (see FIG. 8A) due to the strong bonding of the gas molecules to the active area of the channel 106. This is a known problem of the existing sensors using IGZO as the active layer [4, 6]. The semiconducting channel properties could be revived only after the application of some external energy.

Hence, the inventors explored the recovery of the TFT sensor by using light activation, as the IGZO material is reported to have excellent photoelectric characteristics [7]. Therefore, the inventors have evaluated the IGZO TFT sensor 100's recovery performance after exposure to 5 ppm of the $NO_2$ gas by illuminating the sensor with various commercial light-emitting diodes (LEDs) 703 such as UV LED (400 nm), Blue LED (~450 nm), White LED and Red LED (~635 nm), having the same intensity (~1 mW/cm$^2$), and all of them being mounted at about 2 cm above the active area, as illustrated in FIG. 7. It was found that the gas exposed sensors were completely regenerated after the illumination with only UV, blue, and white light, but not regenerated with the red light. This observation is consistent with the absorbance spectra shown in FIG. 4, which indicates a strong absorbance of the UV and blue wavelengths for the sensor 100, and it is close to zero for the red spectrum.

Figure 9:
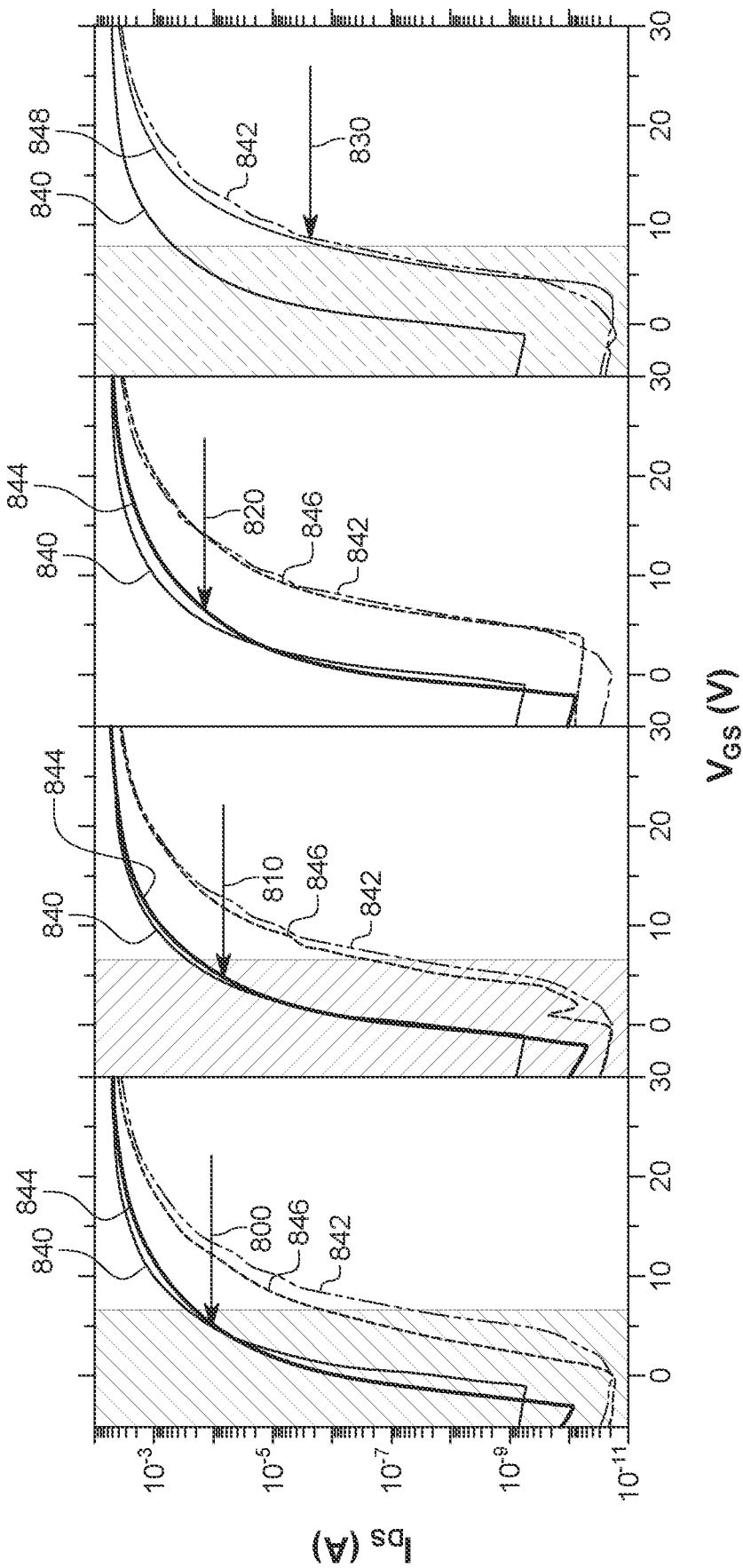
FIG. 9 illustrates the recovery of the IGZO TFT gas sensor, after interacting with the gas, under various light conditions.

The inventors also noted that the recovered sensors responded again to the $NO_2$ gas as the pristine sensors, i.e., no degradation of the sensitivity was observed. In this respect, the corresponding response and revival times are shown in FIG. 9, for the UV 800, blue 810, white 820, and red 830 light. The graph shows the pristine response 840 of the sensor (i.e., no prior gas interaction of the channel region), the gas interaction response 842 after the channel region of the sensor has interacted with the gas and the channel region was not regenerated, the revival response 844 of the active layer after 3 min of UV light exposure, 5 min of blue light exposure, and 10 min of white light exposure, and the sensor's gas response 846 after recovery. FIG. 9 also shows the no revival response 848 of the sensor 100 when exposed to the red light.

Figure 10:
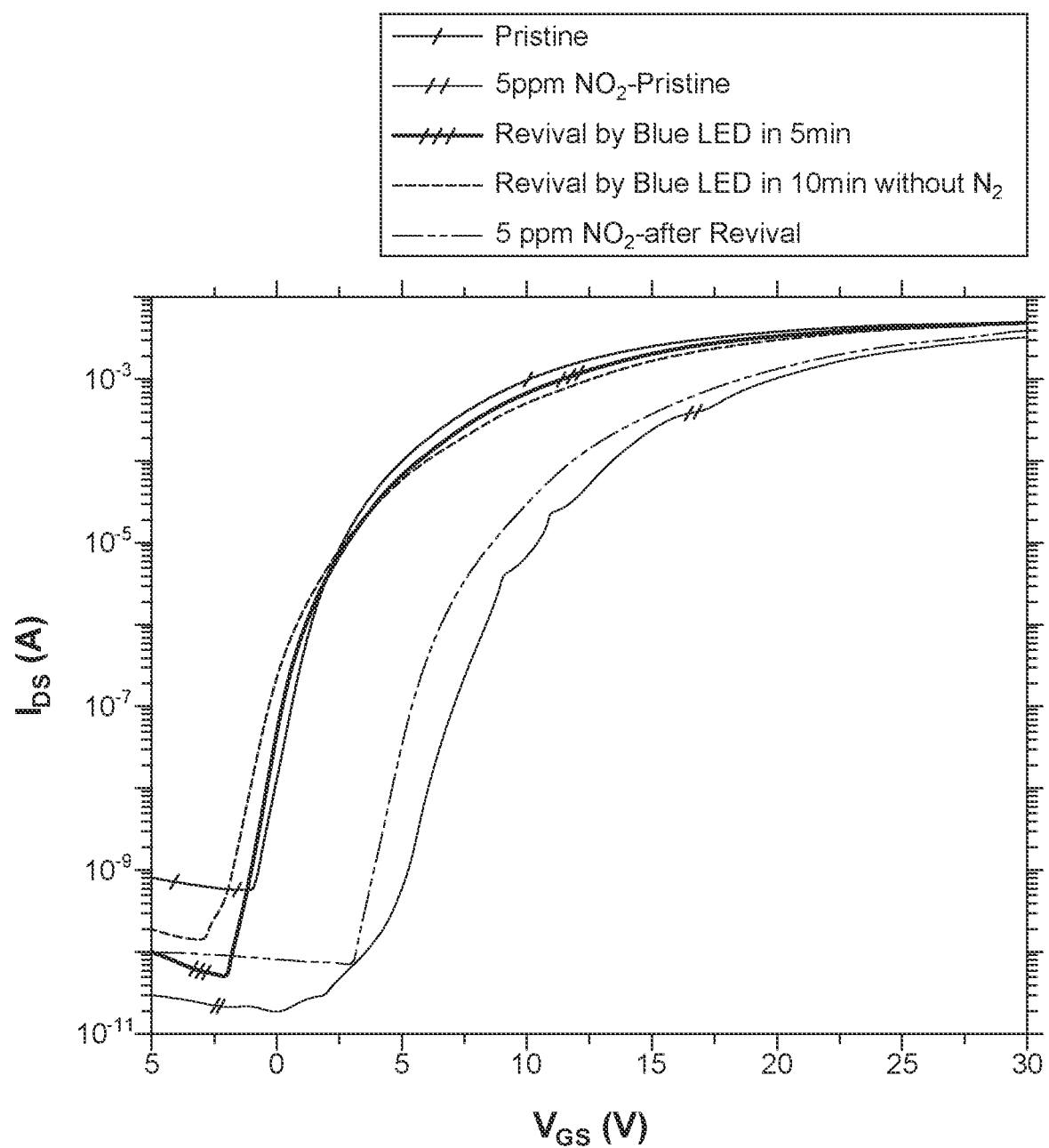
FIG. 10 illustrates the transfer characteristics of the IGZO TFT gas sensor after exposure to a given gas concentration when purged with and without $N_2$.

The inventors also noticed that the recovery time with the UV LED (3 min) was much shorter than with Blue LED (5 min) and White LED (10 min) in the presence of the $N_2$ purge. However, the UV LEDs are harmful to human health and more expensive than the blue LEDs; hence, the rest of the experiments discussed herein were conducted with the Blue LED alone. The light-activated recovery time without the $N_2$ purge was longer than in the presence of the $N_2$ purge during revival, as shown in FIG. 10.

The sensing and recovery mechanisms for the sensors 100 were investigated by the inventors in view of the individual role of the elements that make up the IGZO thin-film 106. This investigation of the individual role of the Indium (In), Gallium (Ga) and Zinc (Zn) in the IGZO TFTs revealed that the concentration of these elements determine the electrical properties of the TFTs due to the electronic band structures in the IGZO composite. In this regard, the In concentration determines the conductivity of the channel 106, the Ga concentration determines the OFF current that can be tuned to control the ON/OFF ratio, and the Zn concentration determines the subthreshold swing of the TFT. The concentration of the In in the IGZO thin-film determines the sensitivity to the $NO_2$ gas at room temperature. A previous study [8] showed that the In concentration in the IGZO composite determined the $NO_2$ absorption at low temperatures. The higher the In concentration, the higher the sensitivity to the $NO_2$ gas in the chemiresistive based sensor at a temperature less than 150° C.

Figure 11:
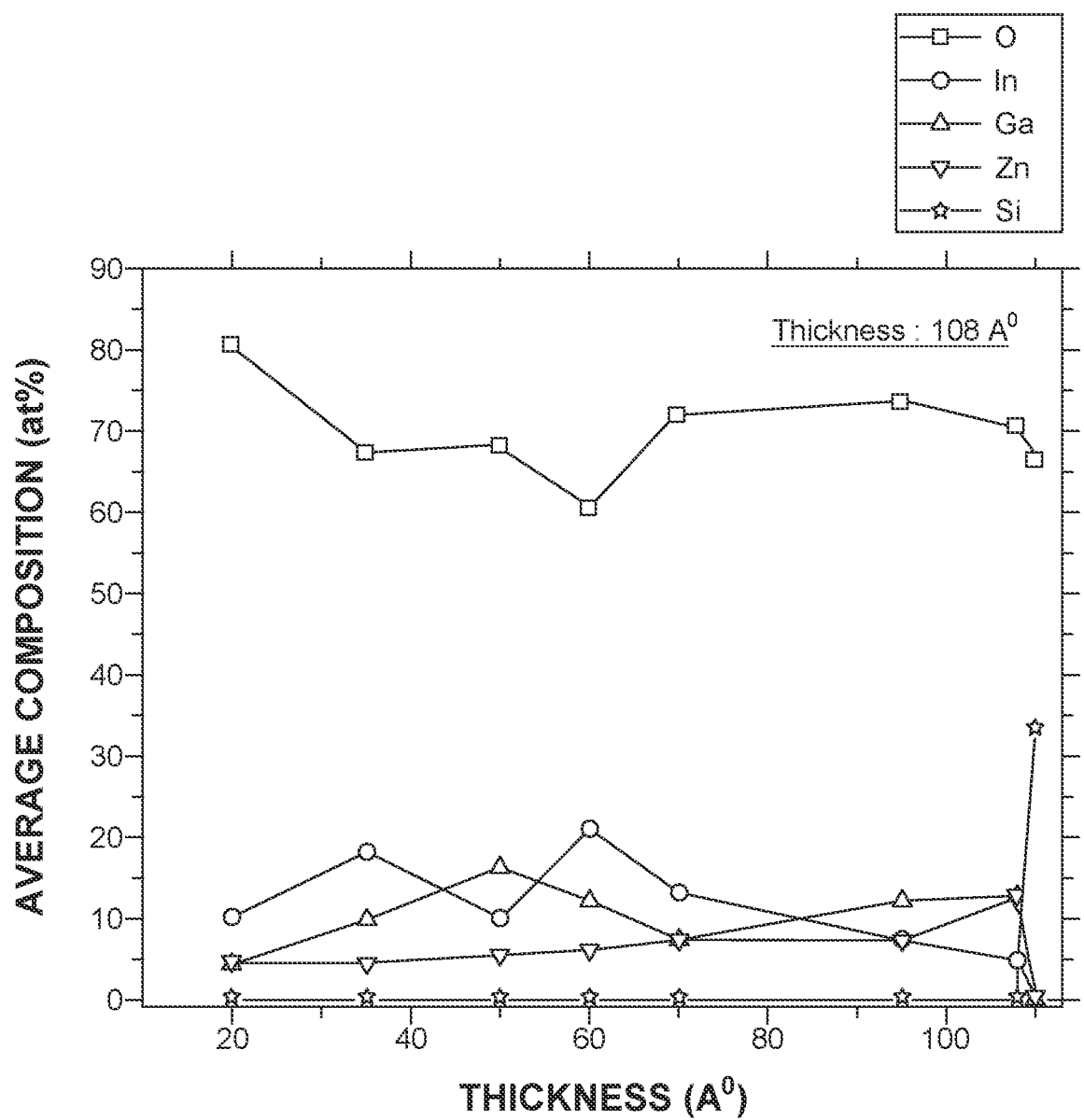
FIG. 11 illustrates the composition of the various components of the IGZO thin-film as a function of a depth of the IGZO thin-film.

In this regard, a high-resolution RBS analysis of the IGZO thin-film 106, was conducted by the inventors, for the precise determination of the depth profile of the various elements of the active IGZO layer used in the sensor 100. The results of this analysis are shown in FIG. 11. The average compositions of the various elements are plotted in this figure versus the depth of the IGZO thin-film 106, for a 10.8 nm thick layer. This analysis indicates that the higher concentrations of In in the thin-film led to an increase in the carrier density, which makes the IGZO TFT sensor more sensitive to the $NO_2$ gas.

X-ray photoelectron spectroscopy (XPS) and Kelvin probe force microscopy analyses were also performed on the IGZO thin-film to understand the effects of the $NO_2$ absorption. Three conditions of vacuum processed IGZO thin-film were used for the XPS studies: a) as-deposited IGZO sputtered film, b) RTP annealed IGZO thin-film (active layer used to fabricate $NO_2$ Sensor) and c) $NO_2$ exposed on RTP annealed IGZO thin-film. When the de-convoluted O-1s peaks of these conditions are compared, which correspond to the oxygen in the lattice (M-O), oxygen deficiencies (M-$O_{Vac}$) (oxygen vacancies) and weakly bonded hydroxyl groups (M-OH), they are found to be centered at the binding energies of 530.3±0.1 eV, 531.3±0.1 eV, 532.3±0.1 eV, respectively. Previous studies have shown that these components reflect the electrical behavior of the IGZO TFTs in terms of the shift in $V_{th}$, ON/OFF current, and field-effect mobility. The M-O peak corresponds to the conducting pathways in the channel and improved mobility of the charge carriers, whereas the M-$O_{Vac}$ peak and M-OH correspond to the carrier concentration, defects, and trap sites in the film. When comparing the areas under O-1s peaks of these conditions, it was observed the improvement in the M-O % and the reduction in M-$O_{Vac}$ and M-OH % after RTP annealing, as compared to the non-annealed device, which indicates a fewer numbers of trap sites and improved carrier density. This reflects a better performance in terms of stability and ON current, which is in line with other studies.

To study the effect of the $NO_2$ adsorption, an XPS analysis was performed on an RTP annealed device after prolonged exposure to the $NO_2$ gas. The O-1S peak after gas exposure shows a decrease in M-O % and a slight increase in both the M-$O_{Vac}$% and M-OH %. Variations in the O-1s peaks indicate an increase in the trap sites and scattering centers within a few nm of the IGZO thin-film, affecting the charge carriers and their mobility. The observed electrical behavior after the $NO_2$ gas exposure, such as the reduced ON current, decreased mobility and positive shift in $V_{th}$, are consistent with the increase in the surface defects.

Figure 12A:
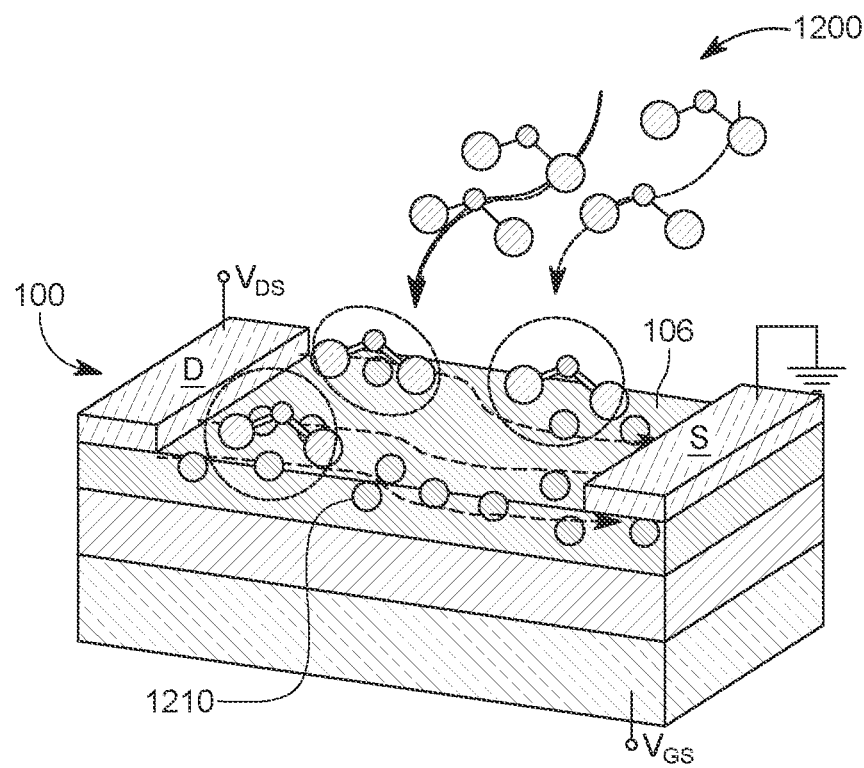
FIGS. 12A to 12C illustrate how the gas interacts with the IGZO thin-film and how the light emitted by an LED device removes the gas from the IGZO thin-film.
Figure 12B:
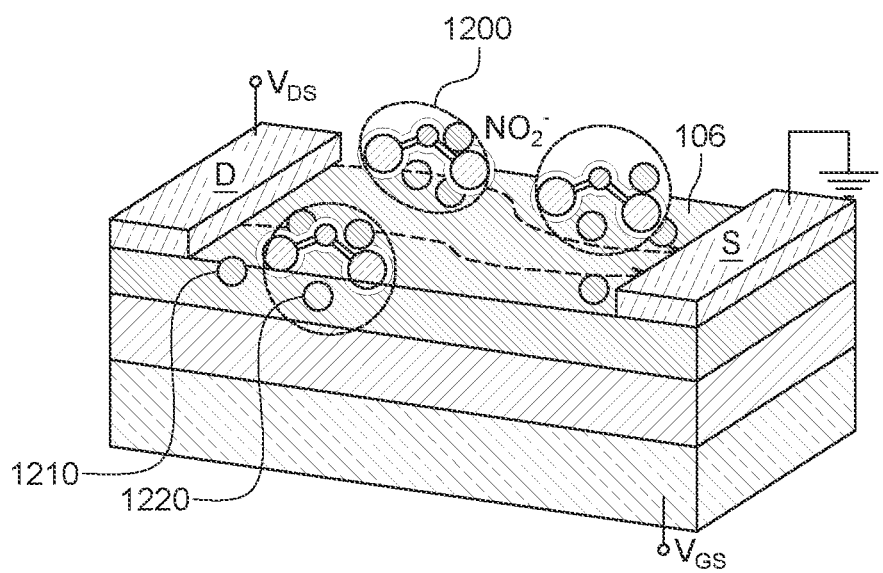
Figure 12C:
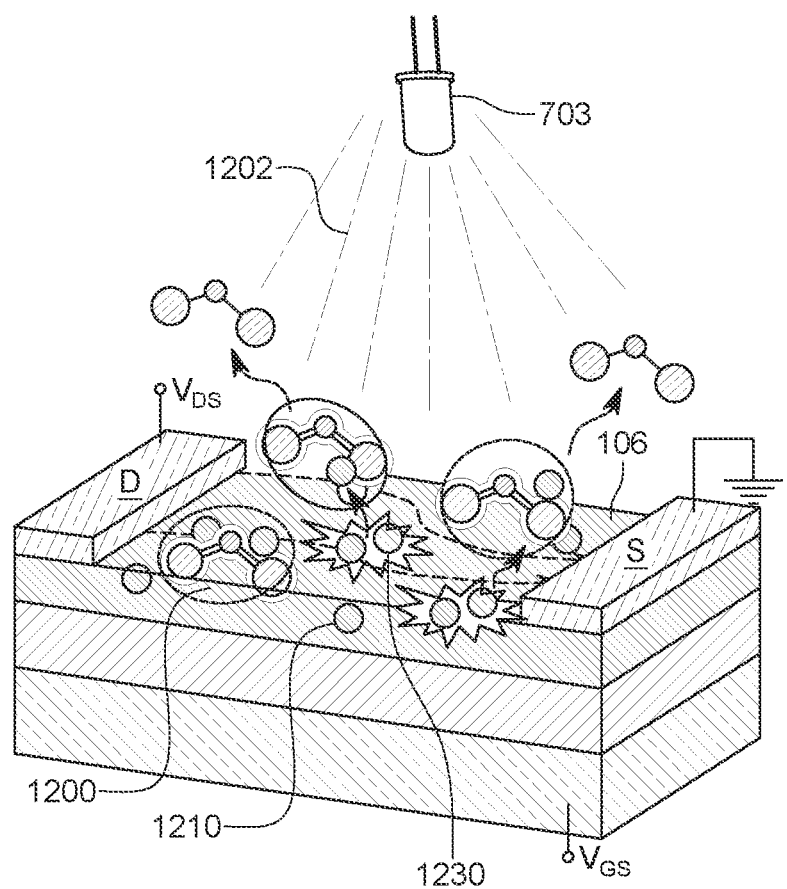

A Kelvin probe force microscopy (KPFM) analysis was also performed to understand the IGZO surface interaction with the $NO_2$ gas. The KPFM images of the pristine IGZO thin-film and of the thin-film immediately after exposure to the $NO_2$ gas show the measured contact potential difference (CPD), which is defined as CPD=$(\phi_{tip}-\phi_{sample})/e$, where is the work function. KPFM scanning was performed over an area of 500 nm×500 nm. It was found that the CPD value increased with the $NO_2$ gas exposure, showing a maximum value at the top and gradually decreasing as scanning progressed to the bottom of the surface due to the desorption of the $NO_2$ molecules. An average CPD value after exposure is considered to be indicative of the work function. A shift in the work function toward vacuum level indicates the presence of a negative charge on the surface due to ionized $NO_2$ molecules ($NO_2^-$). From the KPFM analysis, the inventors concluded that the $NO_2$ molecules 1200 were absorbed on the surface of the IGZO thin-film 106, as depicted in the schematic of the sensor 100 in FIG. 12A. The XPS analysis and electrical characteristics indicate that the adsorbed $NO_2$ molecules 1200 depleted the charge carriers 1210 (see positions 1220 that are indicative of the missing electrons 1210) from the channel 106, as shown in FIG. 12B. However, when the blue light 1202 generated by the blue LED device 703 is turned on to recover the active layer 106, as illustrated in FIG. 12C, pairs of hole-electrons are formed, and the $NO_2$ molecules are removed from the active layer 106 by absorbing one member of the pairs.

In polycrystalline materials or materials with higher effective area, gas molecules diffuse through the grain boundaries where higher temperatures are required for active sensing and recovery. The IGZO thin-film 106 used for the sensor 100 is smooth, with a mean roughness of 0.23 nm, and it is an amorphous semiconductor without grain boundaries. Hence, there is a low probability for gas molecule diffusions. Restricting the gas molecules to the IGZO surface requires minimal energy to desorb them, and thus, it is possible to achieve the recovery with the light from the LED 703 as illustrated in FIG. 12C. Observations of the recovery process with LED 703, after the $NO_2$ gas exposure, suggest that the photo-carrier generation (schematically illustrated in FIG. 12C) plays a large role in regenerating the active layer by desorbing the ionized molecules ($NO_2^-$). The holes 1230 generated in the IGZO thin-film 106 (see FIG. 12C) upon illumination neutralize the ionized molecules ($NO_2^-$) and desorb them from the surface as described by equation (4) below. The presence of the $N_2$ during the recovery helps in sweeping away the desorbed molecules making the recovery time shorter. This desorption mechanism is shown in FIG. 12C, and it is consistent with the reported desorbing of $O_2^-$ molecules on n-type metal oxides and light-activated metal oxide gas sensors. The desorption of the ionized molecules ($NO_2^-$) under light is described by:

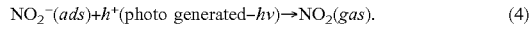

$$NO_2^-(ads) + h^+(\text{photo generated} - hv) \rightarrow NO_2(gas). \quad (4)$$

Figure 13A:
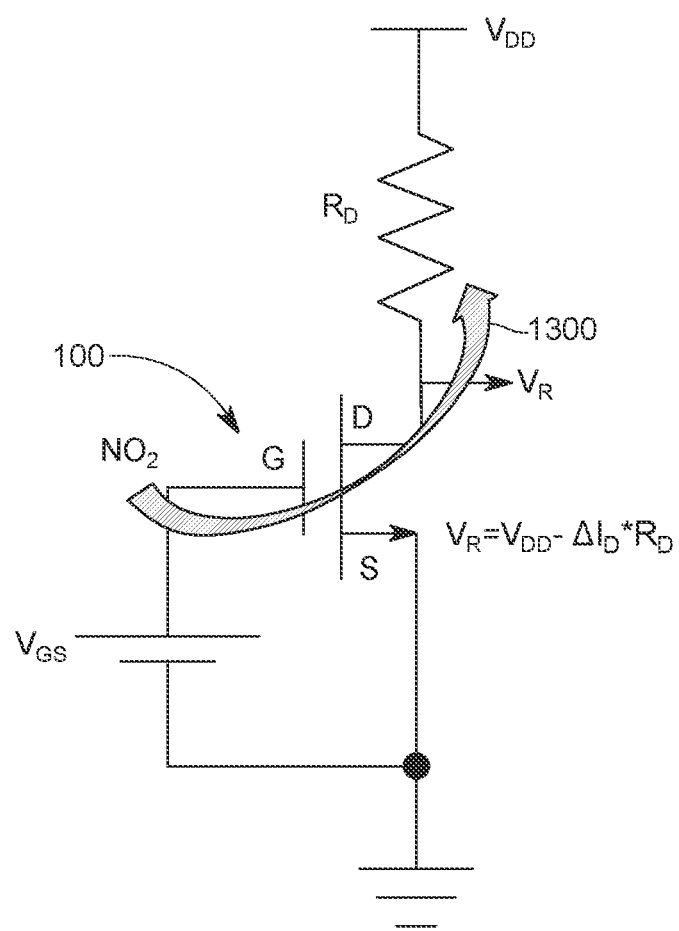

The performance of the IGZO TFT sensor 100 has been investigated in the common source (CS) configuration, as shown in FIG. 13A. The common source configuration is characterized by the gate of the transistor 100 being electrically connected to the source, through a voltage source described by $V_{GS}$ in the figure. Also, a resistor $R_D$ is connected between the drain of the transistor and the power supply $V_{DD}$. The TFT 100 was operated with $V_{DS}=10V$ and $V_{GS}=15V$. In this configuration, the effect on the change in the current $I_D$ was more significant after exposure to the $NO_2$ gas 1300, and measured in terms of the voltage $V_R$ across the resistor $R_D$, which is $V_R=V_{DS}-\Delta I_D R_D$.

Figure 13B:
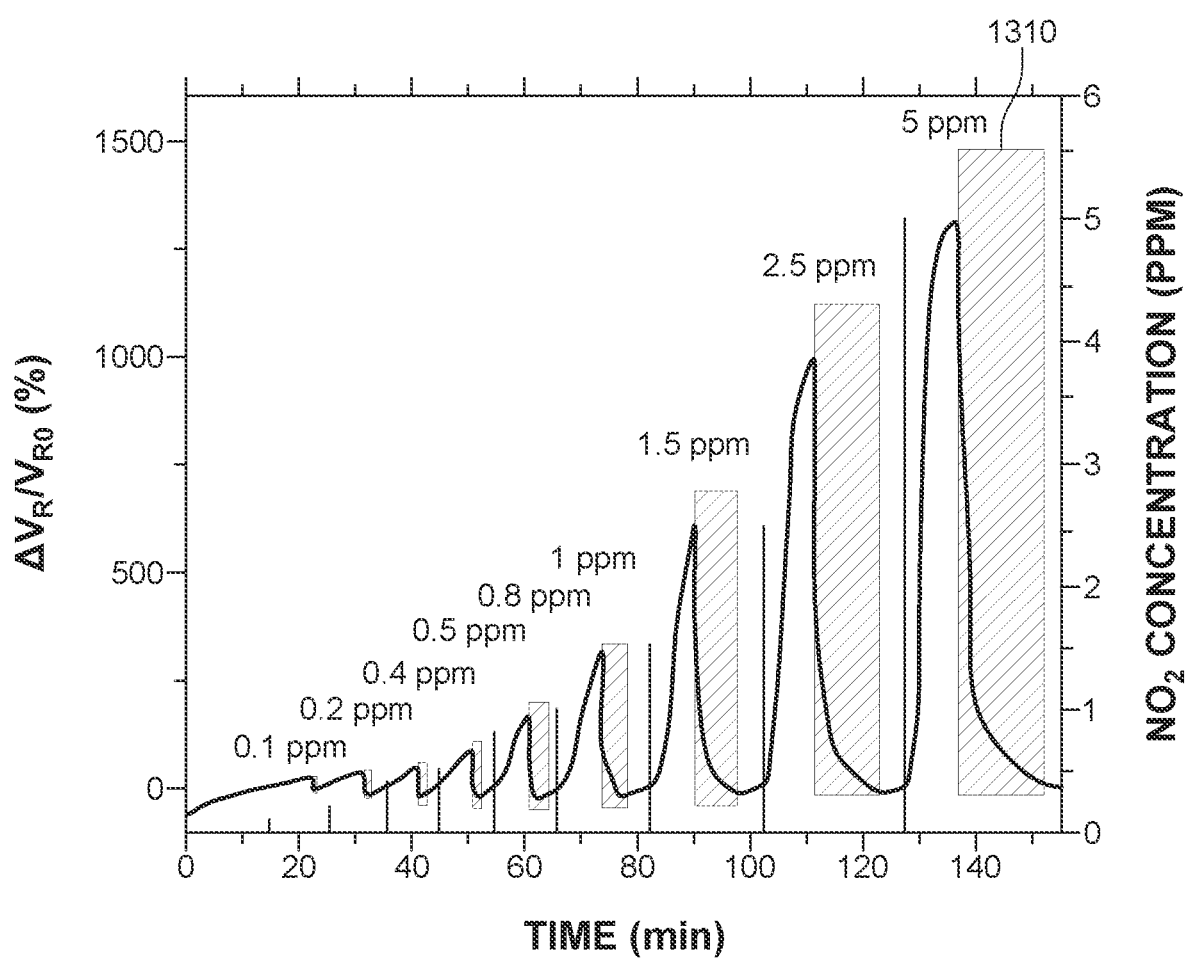
FIG. 13B illustrates the transient response of the IGZO based transistor after a 3 minute exposure to various concentrations of the gas.

In this mode, the transient response of the TFT was acquired for various concentrations of the $NO_2$ gas (from 100 ppb to 5 ppm), as shown in FIG. 13B. The TFT film was exposed to the $NO_2$ gas for 3 minutes in each case. Then, after reaching the saturated response, the TFT film was recovered by being illuminated with the blue light, (which is represented as the shaded region 1310 in FIG. 13B). The recovery time due to the illumination was proportional to the exposed concentration of the $NO_2$ gas, i.e., the higher the concentration due to the exposure, the higher the extent of the electron-hole pair generation required to recover the depleted channel.

The responsivity of the sensor for the 0.1 ppm and 5 ppm concentration exposure to the $NO_2$ gas for 3 minutes was 37% and 1330%, respectively, as also shown in FIG. 13B. A reproducibility study was conducted for 5 ppm of the $NO_2$ gas in the CS configuration and the repeatability response showed that the device was completely recovered by the blue LED, and the response was reproducible at room temperature. The response of the IGZO TFT based sensors when recovered with a high temperature has been shown [4] to decrease after a few cycles due to a partial recovery. In contrast, the sensor 100's response was found to remain stable for multiple cycles when revived with the LED light discussed above. The inventors have also tested the same sensor after 40 days by keeping it in air and the response was the same as that of a pristine sensor, indicating the stability of the sensor in air.

The inventors have found that the fabricated IGZO sensor 100's sensitivity is better than that of the previously reported TFT based $NO_2$ sensors, and the reported MOS devices require either a high temperature (larger than 100° C.) or a complete UV activation for sensing and recovery, whereas the sensor 100 needs only visible light activation, and only during the revival stage.

Figure 14A:
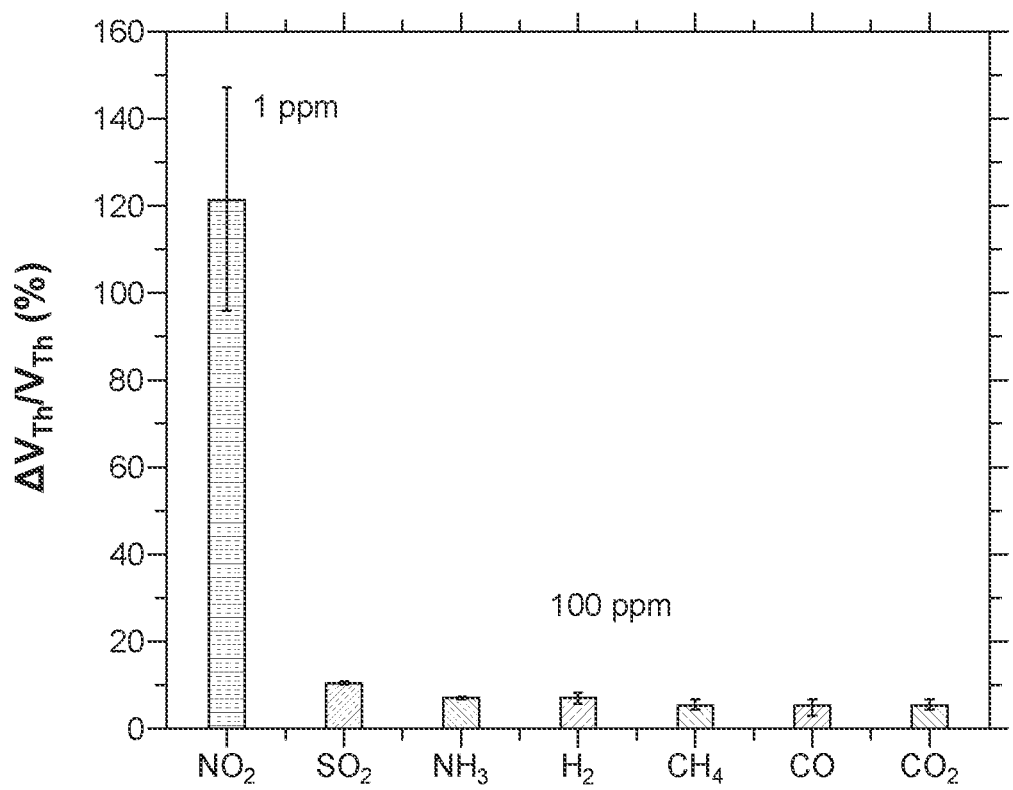
FIGS. 14A and 14B illustrate the variations of the threshold voltage and the drain current of the transistor in response to various gases.
Figure 14B:
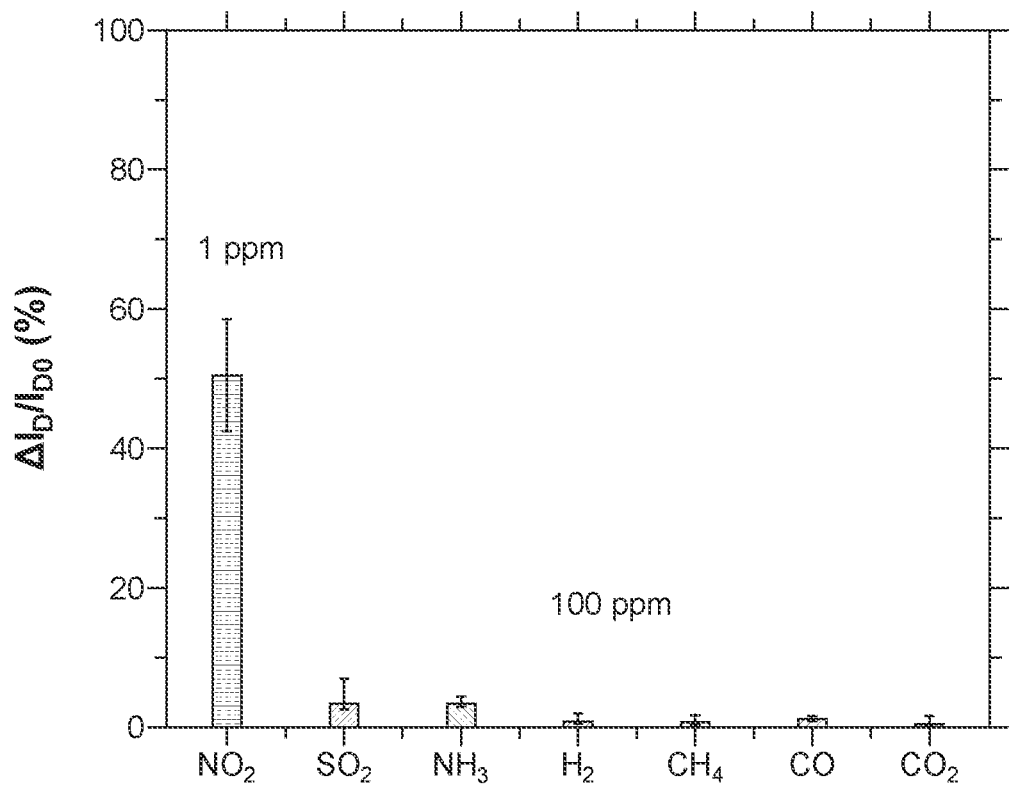

The inventors have also evaluated the IGZO TFTs' response to various harmful oxidizing and reducing gases. The IGZO based sensor 100 was found to be highly selective to the $NO_2$ gas because of its strong oxidizing nature. The response to 1 ppm $NO_2$ was higher than to 100 ppm of other gases, such as sulphur dioxide ($SO_2$), ammonia ($NH_3$), hydrogen ($H_2$), methane ($CH_4$), carbon monoxide (CO), and carbon dioxide ($CO_2$), as illustrated in FIGS. 14A and 14B. Variations in the $V_{th}$ and $I_D$ from the transfer and output characteristics show the high selectivity of the IGZO TFT toward the $NO_2$ gas because of its dominant oxidizing nature, as shown in FIGS. 14A and 14B.

Figure 15:
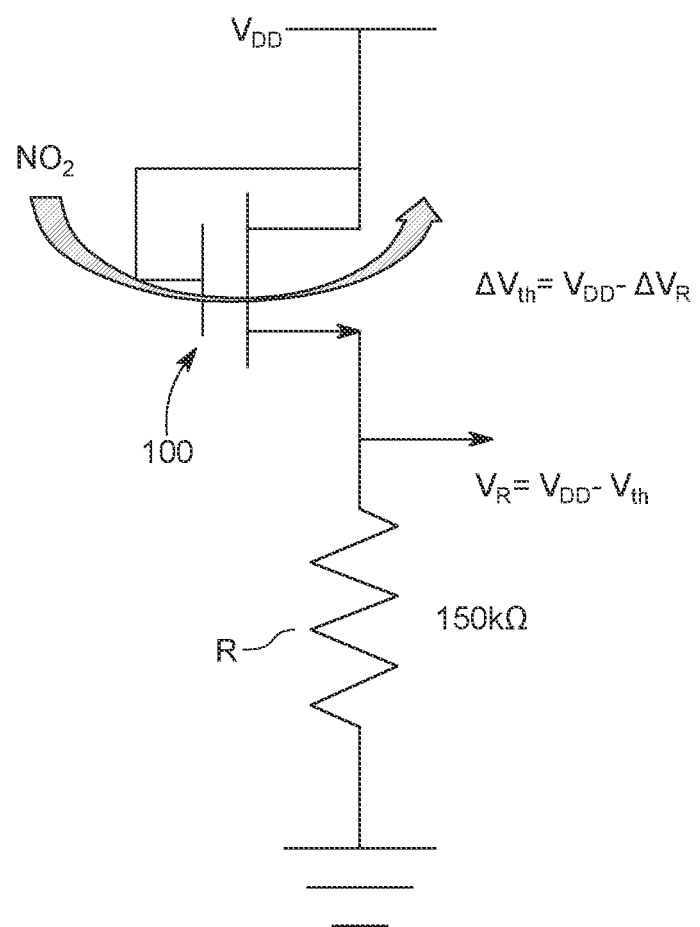
FIG. 15 illustrates a diode-connected transistor configuration of the IGZO based transistor.
Figure 16A:
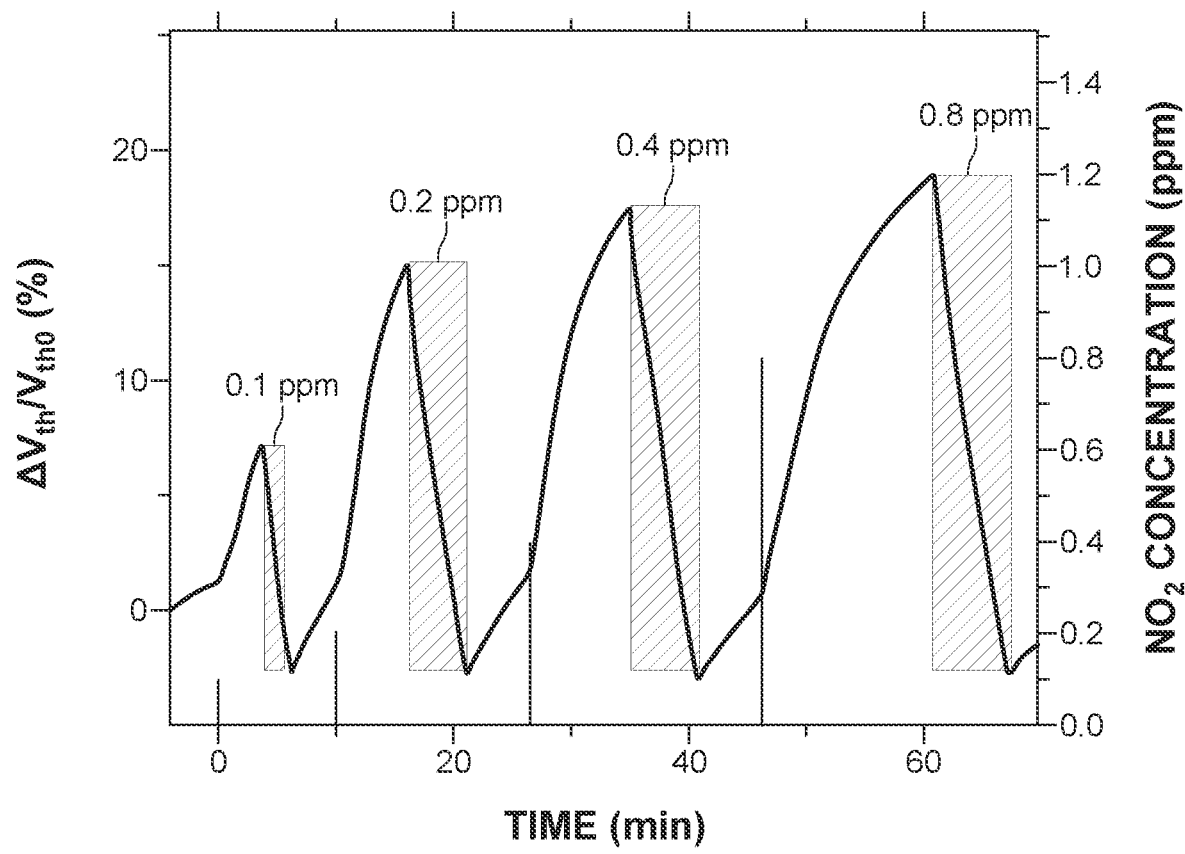
FIGS. 16A and 16B illustrate the transient response of the IGZO based transistor of FIG. 15 after 3 minutes of exposure to various concentrations of the measured gas.
Figure 16B:
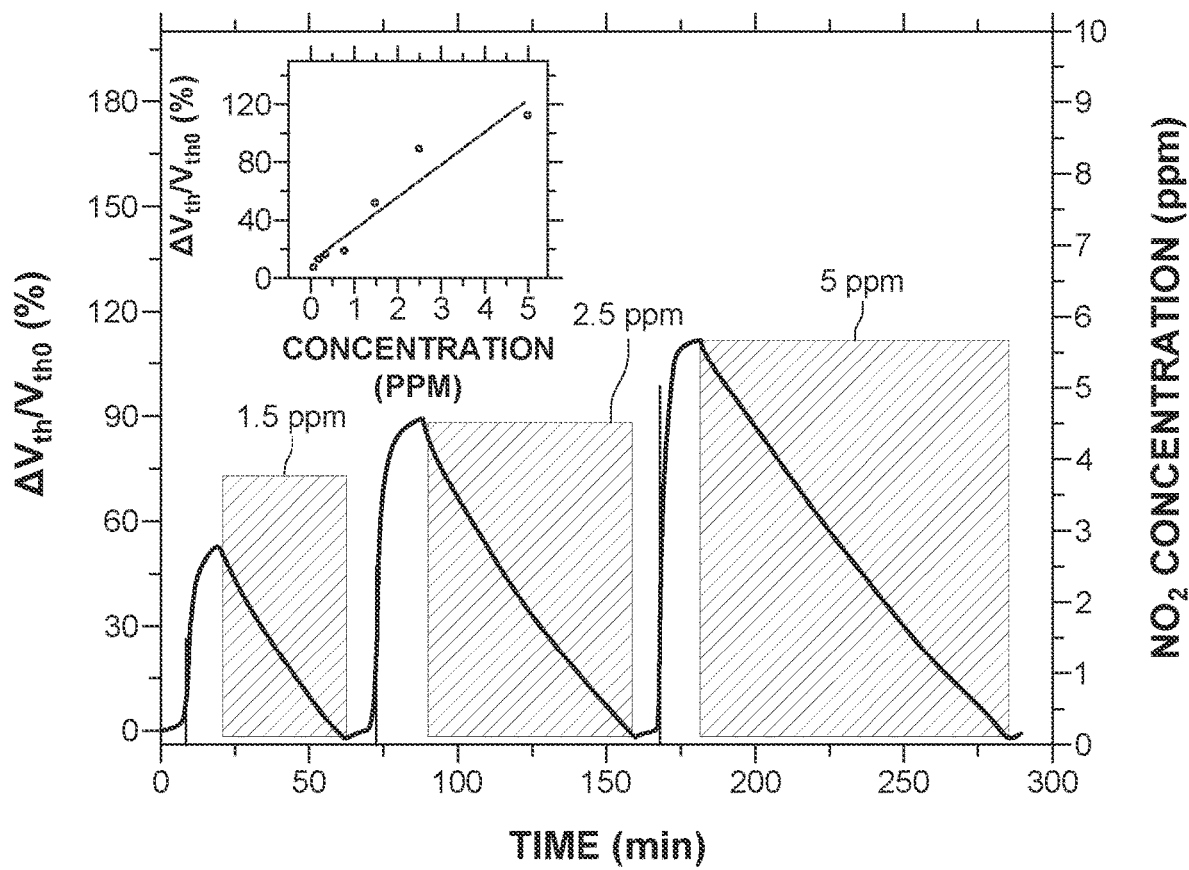

The IGZO TFT sensor 100 was also evaluated in the diode configuration, as shown in FIG. 15, to study the transient variation in the $V_{th}$. In this configuration, which is defined by the gate being electrically connected to the drain and the supply voltage $V_{DD}$, the TFT was operated in saturation ($V_{DD}=V_G=15V$), and the voltage across the resistor R (150 kΩ in this case) is measured with a precision multimeter. The transient analysis was carried out in a similar manner as for the CS configuration of FIG. 13A, and the threshold voltage $V_{th}$ was calculated from the measured voltages (e.g., $\Delta V_{th}=-\Delta V_R$) and it is shown in FIGS. 16A and 16B, for various concentrations (from 0.1 ppm to 5 ppm) of the $NO_2$ gas. The repeatability of the detection for this configuration was carried out for 2.5 ppm of the $NO_2$ gas, and the results showed that the response is consistent and reproducible when the TFT is used for detection multiple times.

Based on the above studies of the IGZO TFT based sensor 100, the inventors have designed an integrated smart sensor system that can be directly integrated with CMOS electronics or Internet of Things (IoT) sensory nodes for measuring gas concentrations. Two different configurations of such a microsystem are now discussed, one of them to be operated in a parallel or flash mode and the other one in a sequential mode. Each configuration includes at least the IGZO TFT based sensor 100, with the IGZO thin-film 106 directly exposed to the environment for interacting with the gas to be measured, and another IGZO TFT based sensor, which has the active IGZO layer passivated, but otherwise being identical to sensor 100. In one application, the active IGZO layer of the other IGZO TFT based sensor is passivated using a chemical vapor deposition of Parylene-C. This passivated sensor serves to make the TFT insensitive to the ambience.

In one application, the passivation of the TFT is achieved by using chemical vapor deposition of Parylene-C (~1.2 µm thick) in a three-chamber system. In the first chamber, the precursor (2.5 g) was heated at 175° C. under vacuum to generate dimeric vapors. The dimeric vapors were cleaved to monomer gas in the second chamber at an elevated temperature of 650° C. In the third chamber, the monomer gas was deposited and self-assembled to form the Parylene-C on top of the $Si/SiO_2/IGZO$ substrate at $10^{-6}$ mBar vacuum level. Other methods that are compatible with the IGZO may be used to passivate the active layer 106 and other materials than the Parylene-C may also be used.

The non-passivated and passivated TFTs allow to design the system with minimal components, no need for analog to digital converters, and readout circuits. In this regard, note that a gas detection sensor, in order to be easily accessible and deployable in a practical environment, needs to be cheap and require a very low amount of energy. The two systems are now discussed in more detail.

Figure 17:
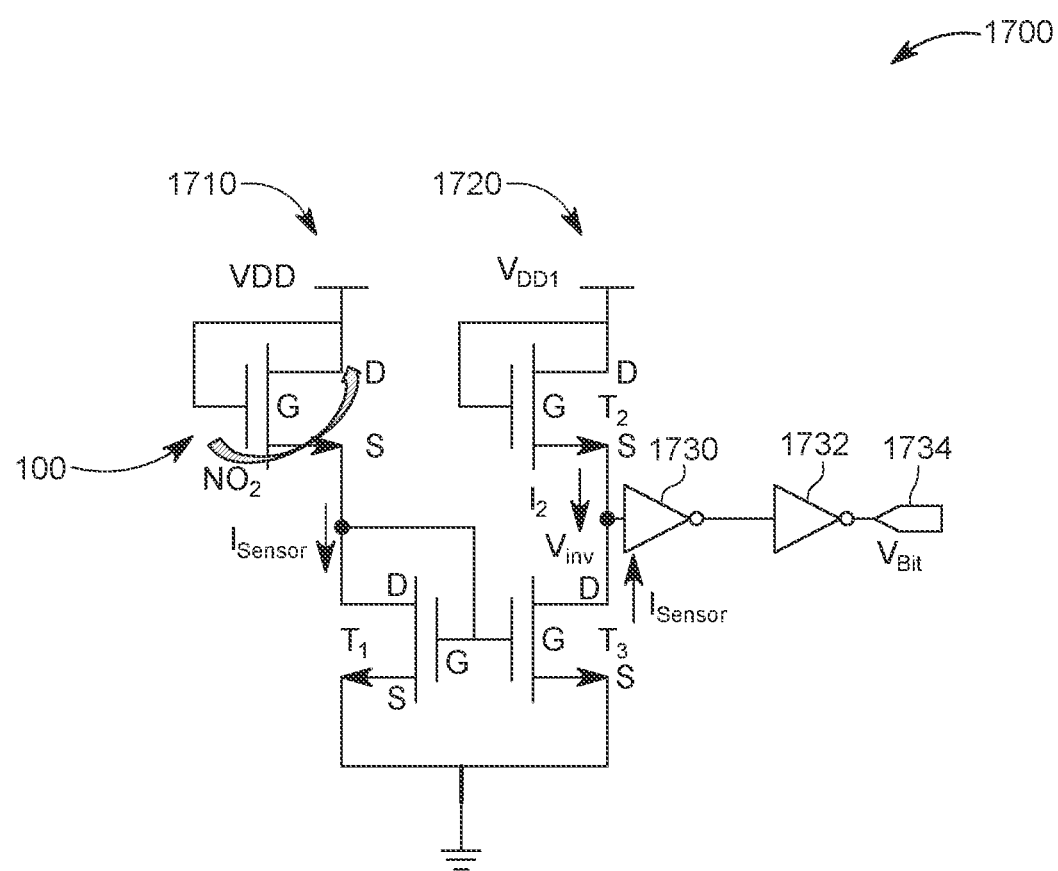
FIG. 17 illustrates a system for measuring the concentration of a gas based on an IGZO transistor.

The first system, or the flash system 1700, is illustrated in FIG. 17 and it can be tuned to simultaneously generate an output represented by plural digits indicative of the $NO_2$ gas concentration detected by the sensor 100. More specifically, as shown in FIG. 17, the flash system 1700 is a current mirror circuit having (1) a master branch 1710 including the IGZO TFT sensor 100 configured in the diode configuration, and (2) a secondary branch 1720 including a passivated IGZO TFT T2 (which is identical to the sensor 100, except for the passivation of the active IGZO layer). The master branch 1710 further includes another passivated IGZO TFT T1 while the secondary branch 1720 further includes a second passivated IGZO TFT T3. The transistors T1 and T3 may be identical to the transistor T2. It is noted that the transistor 100 acts as a sensor because the IGZO thin-film 106 is not passivated while the transistors T1 to T3 cannot act as sensors because their active layer is passivated, i.e., cannot interact with the ambient gas. The sensor 100 is coupled with its drain D to a supply voltage $V_{DD}$ and the sensor T2 is coupled with its drain D to a different supply voltage $V_{DD1}$.

The gates G of the transistors T1 and T3 are coupled directly to each other and to the source S of the sensor 100, as shown in FIG. 17A, to achieve the mirror circuit, i.e., the sensor current $I_{sensor}$ generated by the sensor 100 as a consequence of its interaction with the detected gas ($NO_2$) is mirrored in the secondary branch 1720, and provided at the drain D of the sensor T3. In this way, an inverter logic gate 1730 (called herein the "inverter"), which is connected to the source S of the transistor T2 and to the drain D of the transistor T3, receives the current I2 from the transistor T2 and the current $I_{sensor}$ from the transistor T3. However, the current $I_{sensor}$ is the current generated by the sensor 100 due to the interaction with the detected gas, while the current I2 is the current generated by the transistor T2, which is encapsulated, and thus, it is immune from the interaction with the detected gas. In other words, the inverter 1730 receives the current $I_{sensor}$ that is modified by the detected gas and the current I2, which is not modified by the detected gas, and by comparing these two currents, which are generated by identical transistors, it is possible (through prior calibration) to estimate the concentration of the detected gas. In this sense, as discussed above with regard to FIGS. 8D and 8E, both the threshold voltage Vth and the drain current $I_D$ of the sensor 100 are proportionally affected by the concentration of the detected gas. Thus, by choosing one of these parameters, for example, the drain current, and monitoring its deviation from the current of the encapsulated transistor, it is possible to determine the concentration of the gas interacting with the non-encapsulated sensor 100.

Figure 18:
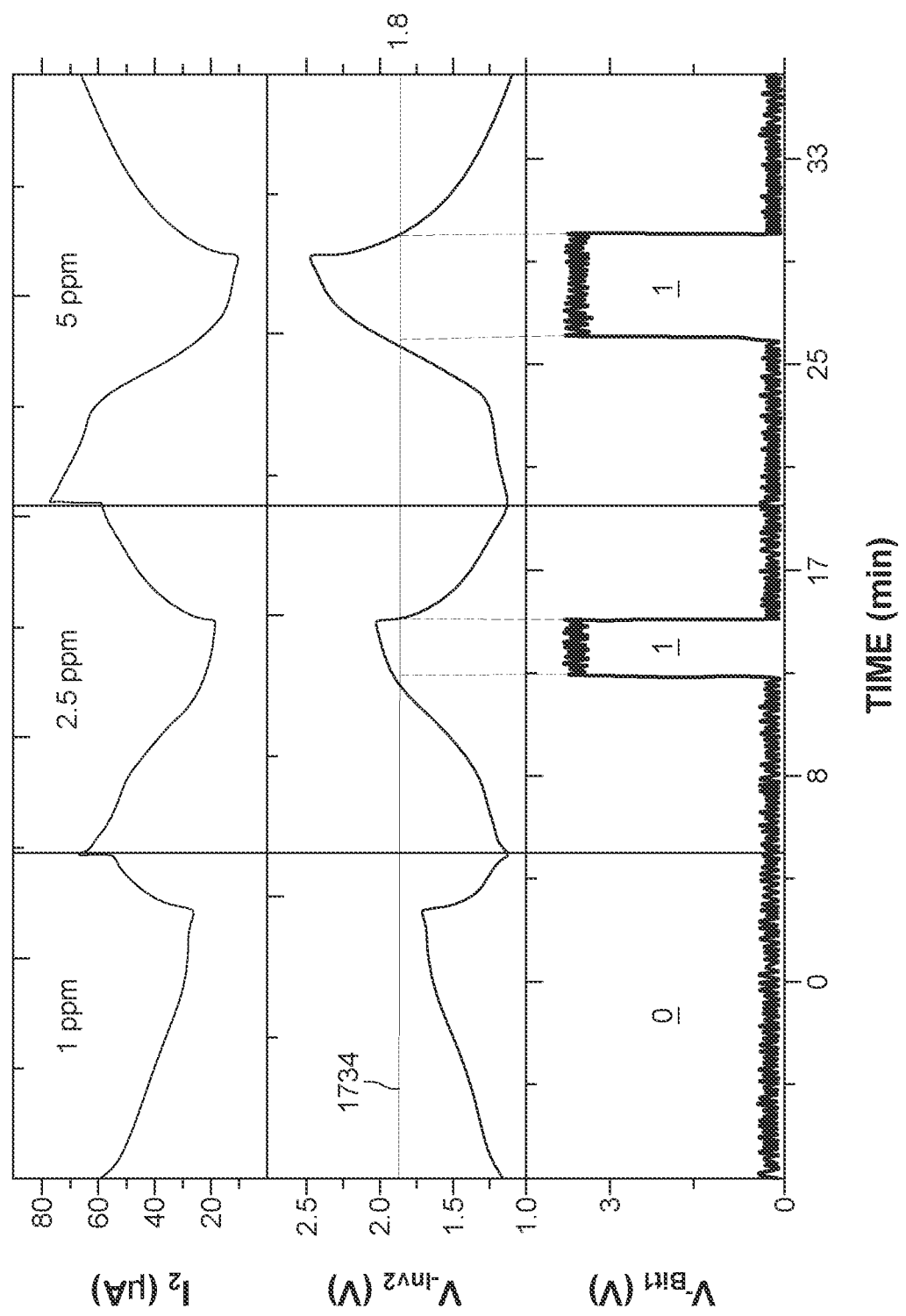
FIG. 18 illustrates the bit response of the system shown in FIG. 17.

In other words, the master branch 1710 controls the current in the secondary branch 1720, and thus, the current $I_{sensor}$ in the master branch will decrease with the increase in the $NO_2$ gas concentration, as observed in the diode configuration and the CS configuration. The $I_2$ is the current in the secondary branch, which is dependent on the $I_{sensor}$ and the $V_{DD1}$ supply. By holding the $V_{DD1}$ constant, the current $I_2$ will be only dependent on the current $I_{sensor}$. Thus, the inverter 1730 would be able to monitor the changes in the current $I_{sensor}$, as the current I2 is constant. FIG. 18 shows that with the increase in the concentration of the $NO_2$ gas, from 1 ppm, to 2.5 ppm to 5 ppm, the current $I_2$ is decreasing, and the correspondingly voltage V-Inv2 at a second inverter 1732 input is increasing. Note that the second inverter 1732 is connected to the output of the first inverter 1730 to produce a more clearer indication about when the sensed current $I_{sensor}$ changes relative to the current $I_2$, i.e., when the current is above a given threshold and also to generate digital bits where the 1s correspond to a high voltage, and the 0s correspond to a low voltage.

In this regard, the voltage supply $V_{DD1}$ at the secondary branch 1720 can be used to tune the baseline of the current $I_2$ and the input inverter voltage, so that the voltage $V_{DD1}$ triggers, in one example, the transition in the inverter for the response proportional to 1 ppm $NO_2$. The output of the second inverter is high only if the $NO_2$ gas concentration is greater than 1 ppm. Due to the $NO_2$ gas sensitivity of the TFT sensor 100 in the master branch 1710, the current $I_2$ will decrease such that the input voltage at the first inverter 1730 exceeds its output high logic value, which makes the output of the second inverter logic high. In one application, a hex-inverter may be used in the microsystem 1700.

FIG. 18 shows that when the voltage received by the second inverter 1732 is below a given threshold 1734 (e.g., 1.8 V), a digital 0 is generated as the output of the second inverter 1732, as shown in FIG. 18 for the situation corresponding to the 1 ppm. However, when the voltage is above the given threshold 1734, a digital 1 is generated, for example, for the situations shown in FIG. 18 as corresponding to 2.5 ppm and 5 ppm. The supply voltage $V_{DD1}$ to the secondary branch 1720 may be selected to make the inverters output a digital 1 at any desired concentration in ppm of the $NO_2$ gas, not only the 1 ppm. For simplicity, this embodiment has been discussed for a 1 ppm threshold. However, those skilled in the art would understand that by changing the supply voltage $V_{DD1}$, any concentration in ppm of the $NO_2$ gas may selected to be the threshold between the 0 and 1 bits.

Figure 19:
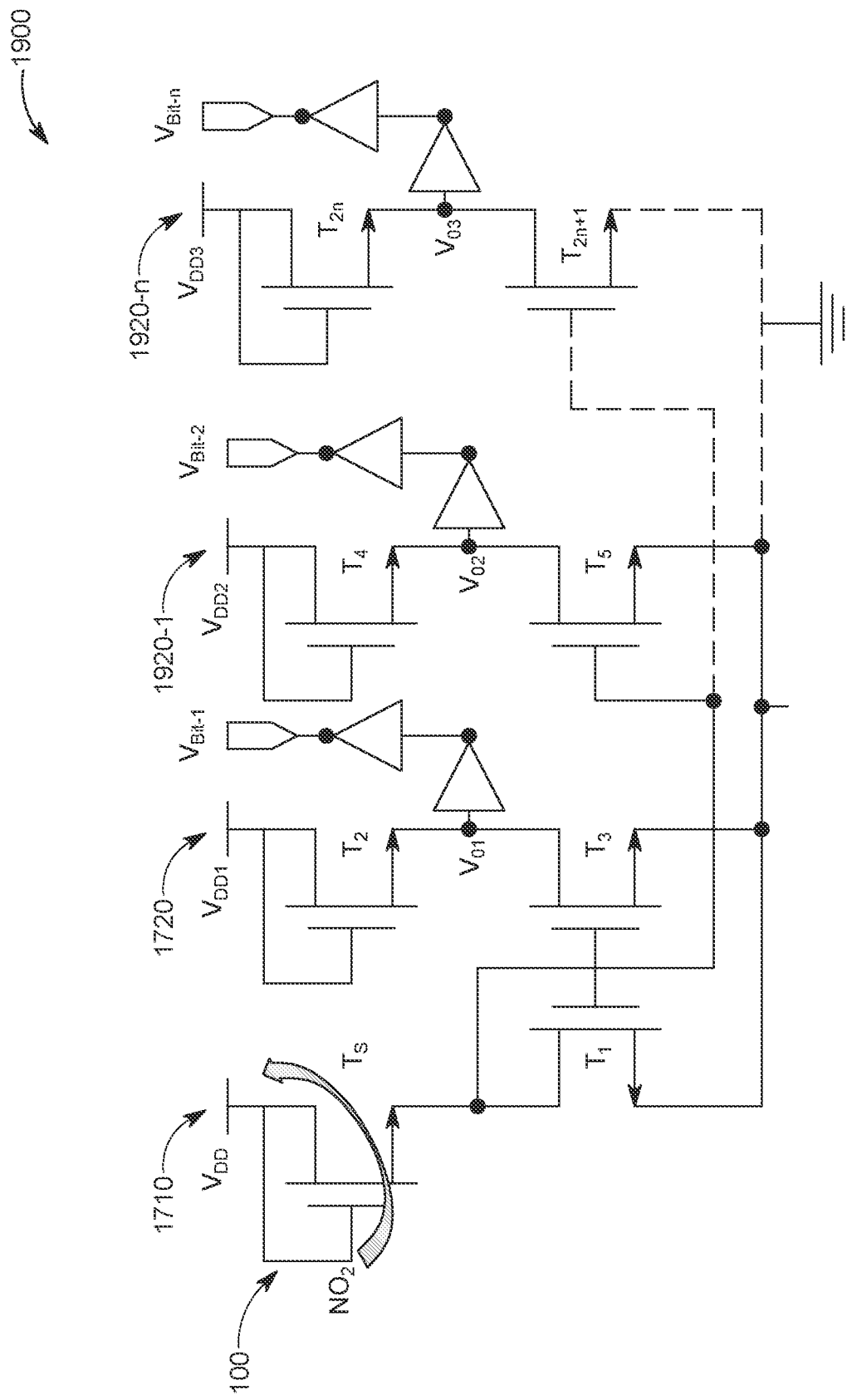
FIG. 19 illustrates a multibit system, which is an extension of the single-bit system shown in FIG. 17, for measuring the concentration of a gas based on the IGZO transistor by simultaneous bit generation.

While the detection system 1700 illustrated in FIG. 17A was designed to produce a zero value when the $NO_2$ gas concentration is below a given threshold, and a one value when the gas concentration is above the given threshold, it is possible to use the IGZO sensor 100 in an improved system 1900 to obtain a n-bit digital output that offers a higher resolution of the gas concentration, as now discussed with regard to FIG. 19. The system 1900 has in addition to the master branch 1710, and the secondary branch 1720 of the system 1700, more secondary branches 1920-1 to 1920-n, where n is any natural number equal to or larger than 1. Each secondary branch 1920-n has the same configuration as the secondary branch 1720, i.e., all the transistors T4 to $T_{2n+1}$ are encapsulated IGZO TFT, and all the gates of these transistors are connected to each other and all their sources are connected to ground. Thus, for the n-bit digital output of the system 1900, there is a need of 2n+1 passivated TFTs and one TFT sensor 100.

Figure 20:
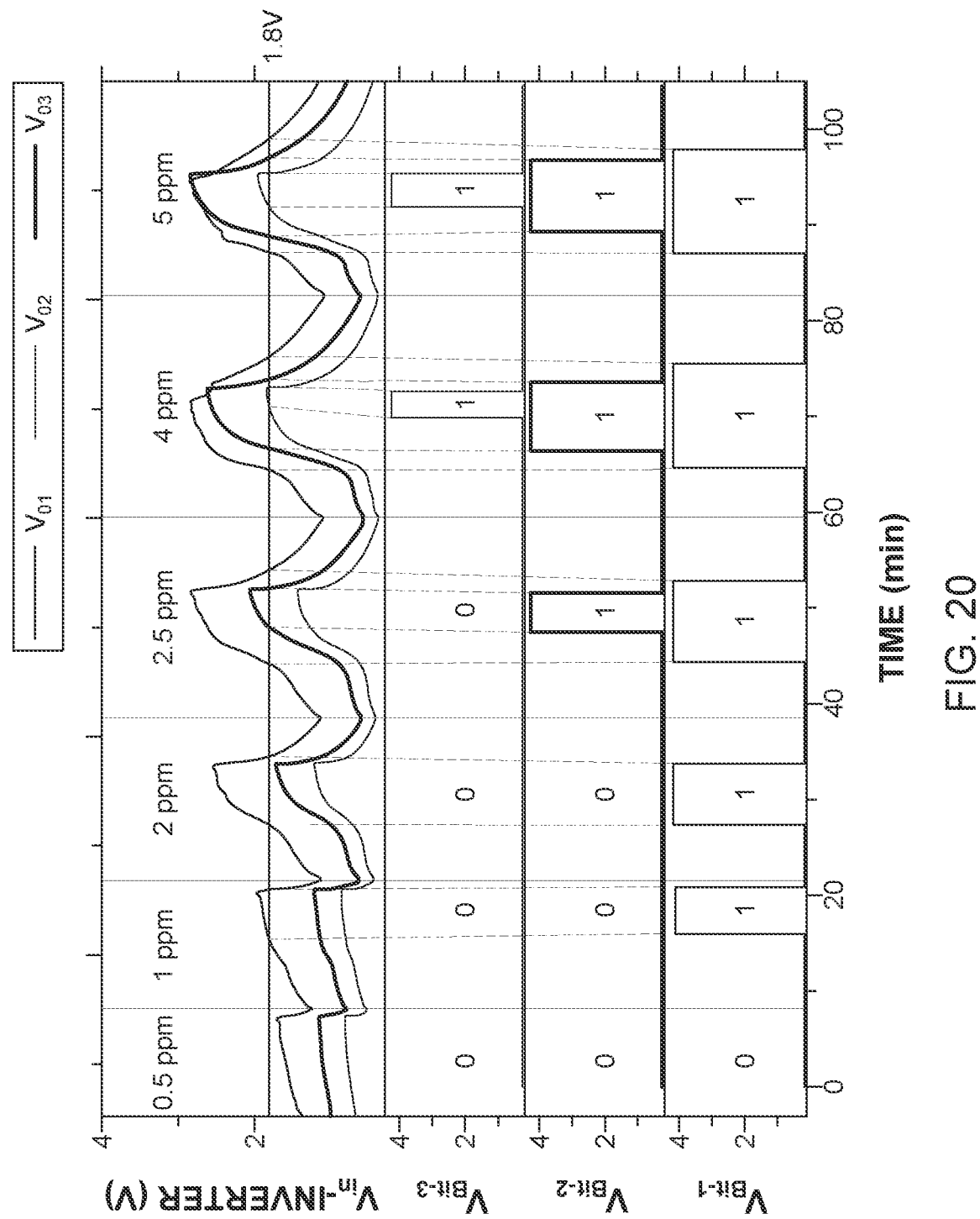
FIG. 20 illustrates the multi-bit response of the system shown in FIG. 19.
Figure 21:
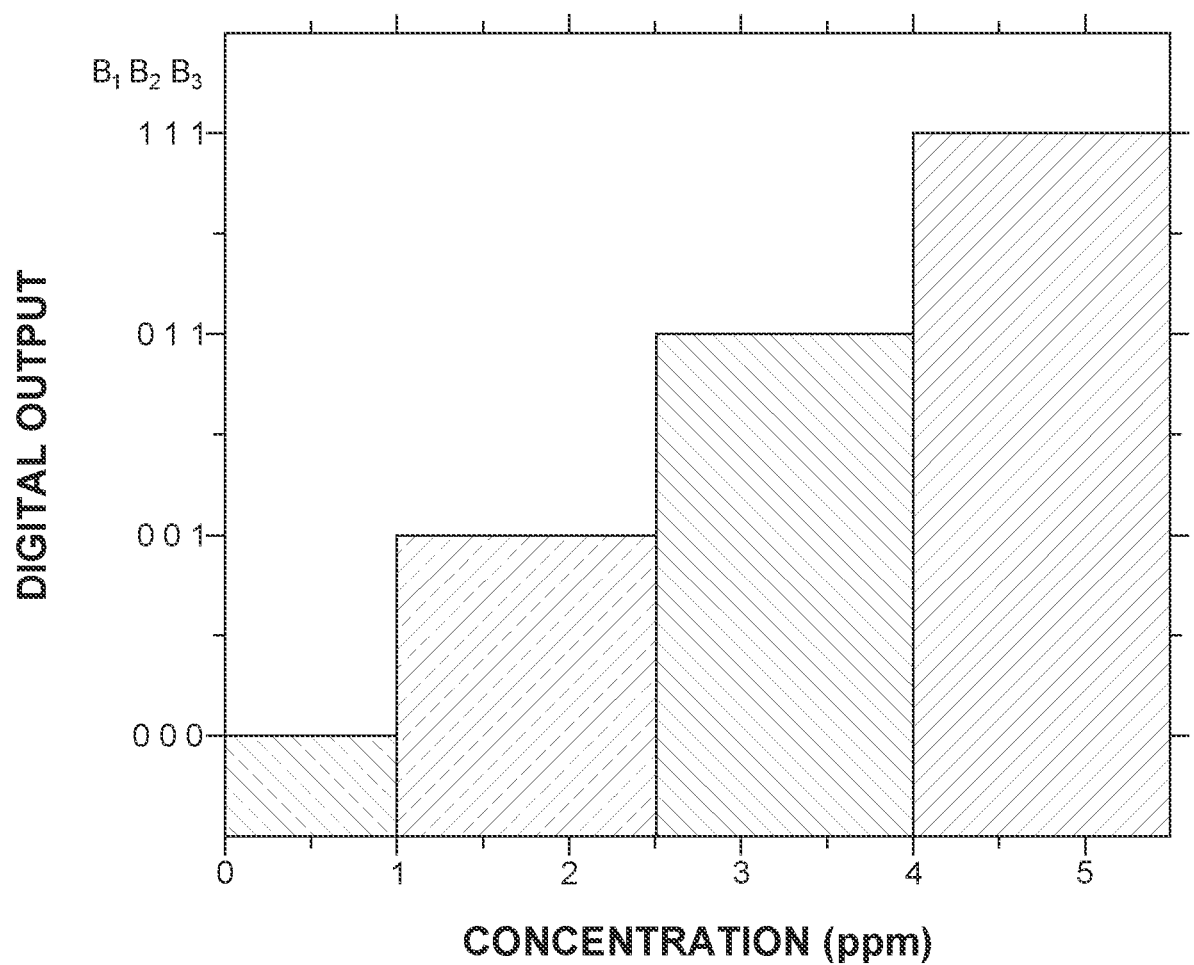
FIG. 21 illustrates the various concentration ranges of the detected gas with the system of FIG. 19.

As a practical implementation, the system 1900 was configured as a 3-bit microsystem, as illustrated in FIGS. 20 and 21. Any number of bits may be used for the system 1900, depending on the desired accuracy. The integrated system 1900 quantifies the $NO_2$ gas concentration and gives a 3-bit thermometer code. The first branch is the master branch with the IGZO TFT sensor that controls the current in rest of the three secondary branches. Voltages $V_{DD1}$, $V_{DD2}$, $V_{DD3}$ are tuned to make the transition at the inverter's output for the $NO_2$ gas concentrations of 1, 2.5 and 4 ppm respectively (which are illustrated in FIG. 21). Note that each of the secondary branches has its own inverter(s). In one application, it is possible to have the same $V_{DD}$ for all the branches, but to have different constant current or reference current values, the upper encapsulated transistors in the secondary branches have to have different dimensions (width and/or length). This is so because the various lengths and/or widths of the upper transistors result in different reference currents in each of the secondary branches of the circuit.

A transient analysis was carried out with the integrated system 1900 in the gas chamber 702 (see FIG. 7) and the system 1900's response was evaluated from 0.5 ppm to 5 ppm $NO_2$ gas concentrations for 3 minutes. The sensor 100 was regenerated with the blue LED, as discussed in the preceding embodiments. FIG. 20 shows the voltages at the first inverter's input node varying with the $NO_2$ gas concentration, and the corresponding digital output at three second inverters ($V_{Bit-1}$ to $V_{Bit-3}$) corresponding to each secondary branch. It is noted that the three thresholds gas concentrations set up by adjusting the supply voltages $V_{DD1}$, $V_{DD2}$, $V_{DD3}$ were 1, 2.5, and 4 ppm (see FIG. 21). Thus, whenever a secondary branch detected a voltage that is higher than the voltage associated with the set up gas concentration thresholds, the output $V_{Bit}$ was 1, otherwise 0. This means that the system 1900 produced the following results; 000, 001, 011, and 111, corresponding to the inverters of the three secondary branches, and each sequence of bits corresponds to a different gas concentration. The 3-bit digital output of the microsystem 1900, which is shown in FIG. 21, quantifies the $NO_2$ gas concentration without any need of a sensor readout and ADC circuits. Thus, this configuration of the system 1900 makes it easy to plug and play the microsystem in any sensing system. One skilled in the art would understand that by having fewer or more secondary branches, the accuracy of the measured gas concentration can be adjusted as desired.

Figure 22A:
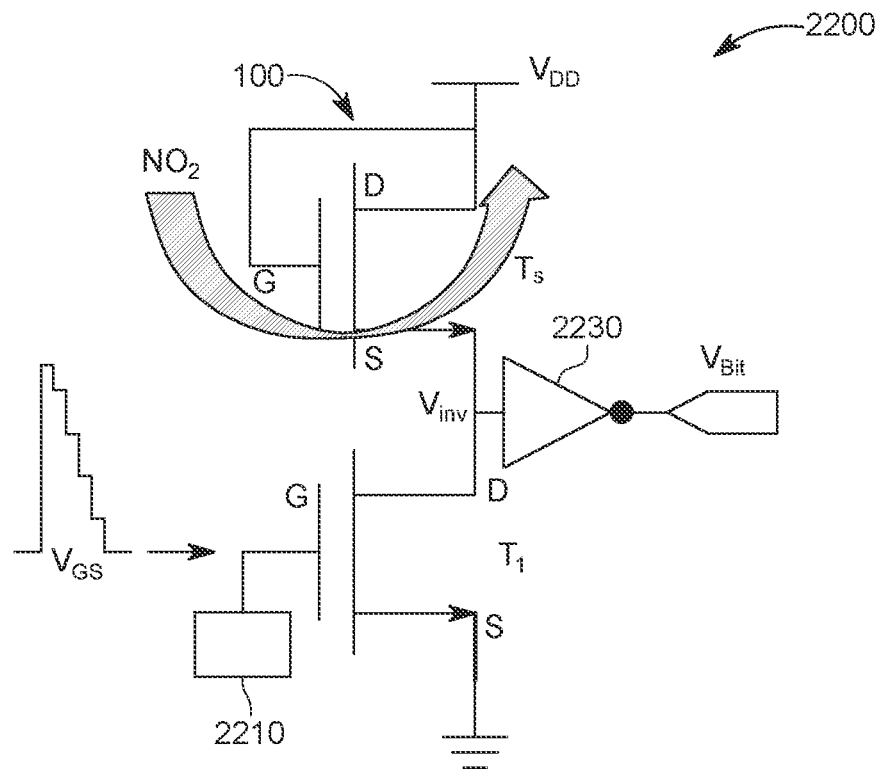
FIG. 22A illustrates another system for measuring the concentration of a gas based on the IGZO transistor by sequential bit generation and FIG. 22B illustrates its physical configuration.
Figure 22B:
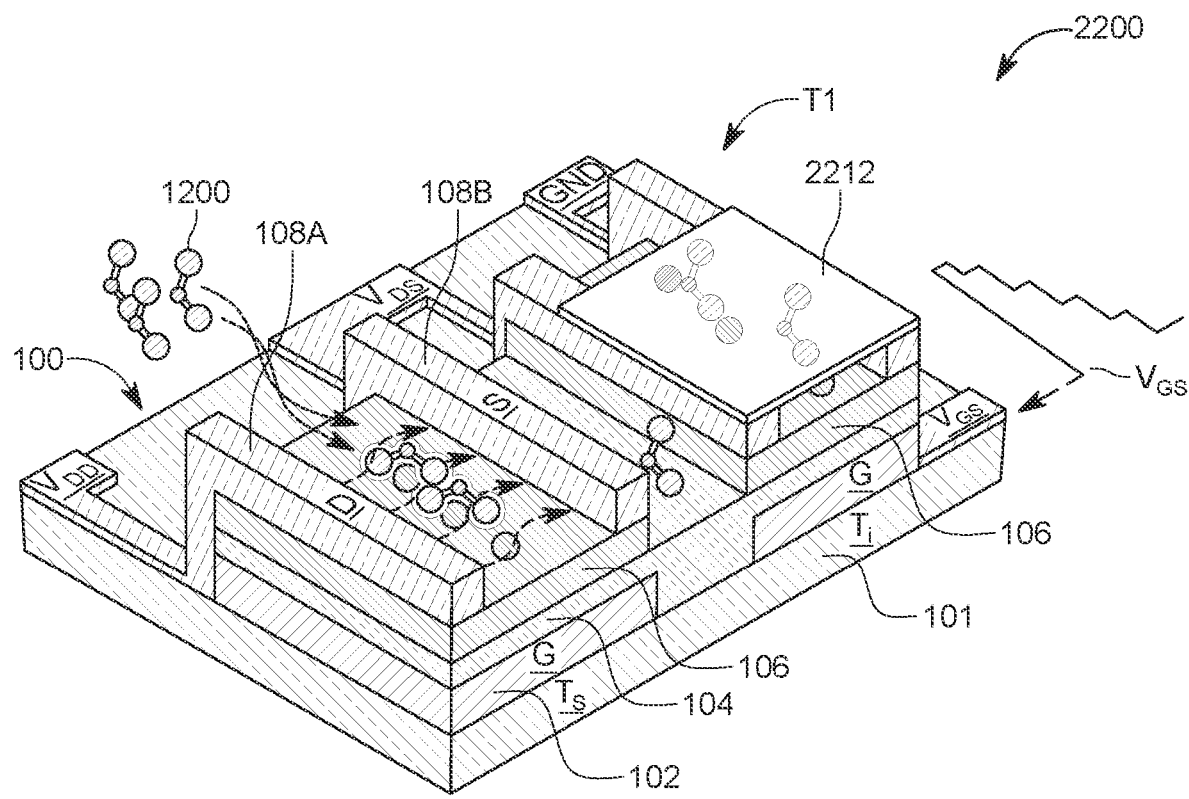

A different system 2200 is now discussed with regard to FIGS. 22A and 22B, and this system, called herein a sequential system, is configured to detect the $NO_2$ gas concentration and digitally quantify its value. The system 2200 sequentially determines each digit associated with the $NO_2$ gas concentration, i.e., if the overall digital code associated with the $NO_2$ gas concentration is 101, the system first determines the first digit 1, then the second digit 0, and then the third digit 1. In this configuration, the IGZO TFT sensor 100 in the diode configuration is cascoded with a passivated TFT T1, as shown in FIG. 22A. The TFT sensor 100, which is at constant bias, controls the current in the branch based on the ambient conditions, whereas the passivated TFT T1 is operated with the specific gate voltage ($V_{GS}$), which maintains the constant current level in the branch. By tuning the $V_{GS}$ voltage of the passivated TFT T1, the base current in the branch can be maintained at different levels, and thus, the voltage ($V_{inv}$) at the input of the inverter 2230 node can be tuned as desired. FIG. 22B shows the actual structure of the sensor 100 and the passivated TFT T1, where the un-passivated sensor 100 and the passivated transistor T1 are shown formed on the same substrate 101. The passivated transistor T1 has the same structure as the sensor 100, except for the Parylene-C layer 2212, which fully covers the active layer 106.

Figure 23:
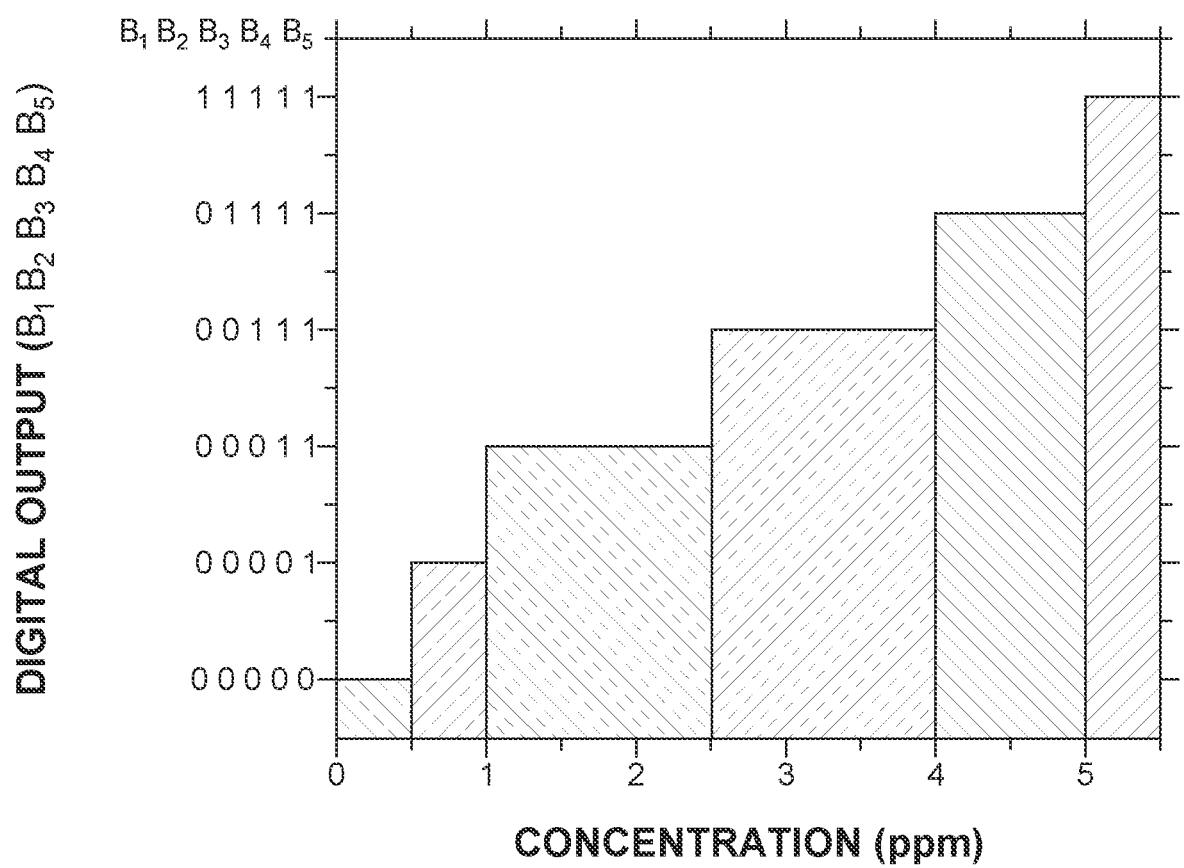
FIG. 23 illustrates the various concentration ranges of the detected gas with the system of FIGS. 22A and 22B.
Figure 24:
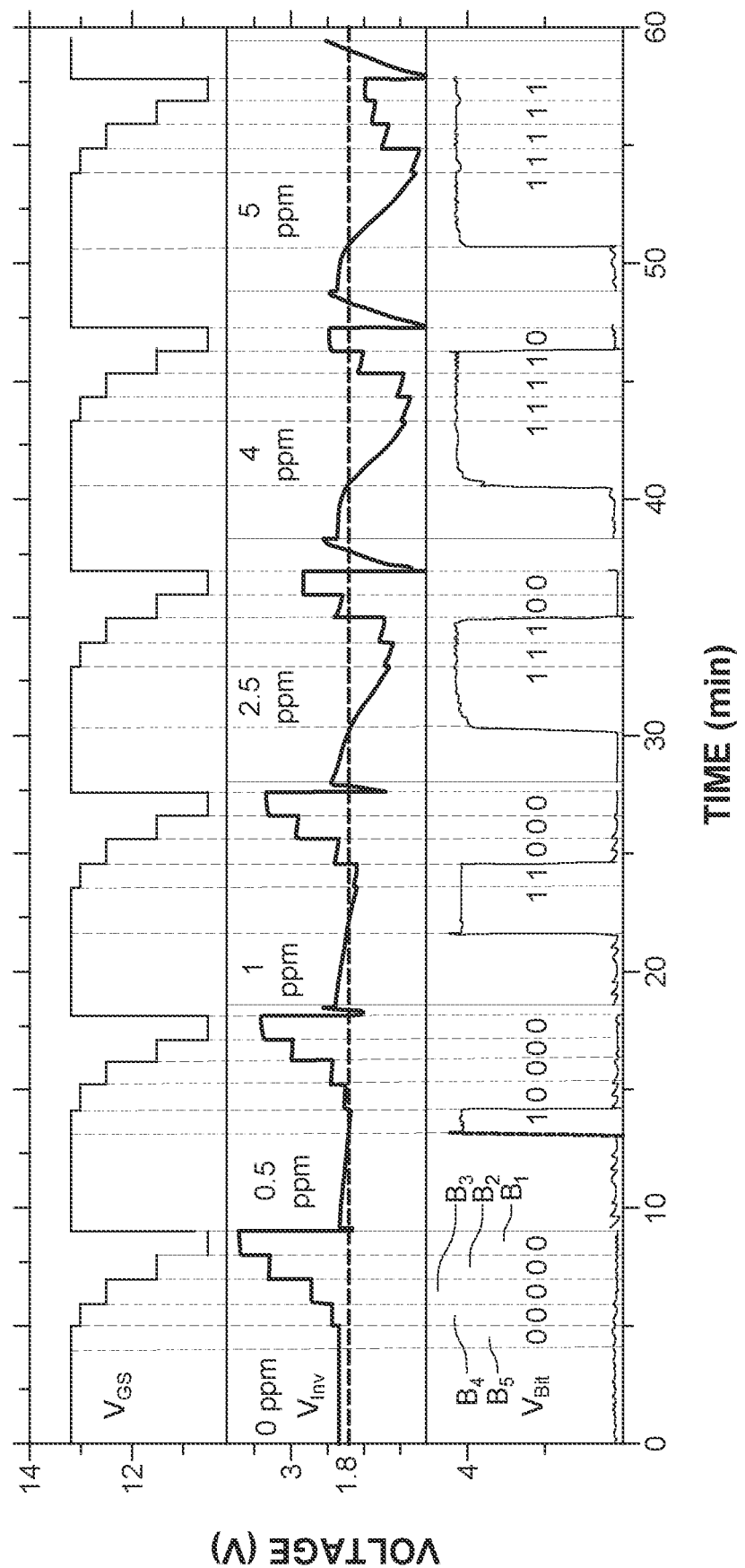
FIG. 24 illustrates the multi-bit response of the system shown in FIGS. 22A and 22B.

The change in the $NO_2$ gas concentration at the sensor 100 induces changes for the $V_{th}$ and $I_D$ of the TFT based sensor 100, and the $V_{inv}$ changes correspondingly. The inverter 2230, when receiving a voltage that depends on the voltage generated by the sensor 100 and the constant voltage generated by transistor T1, is calibrated to generate a logic high when the measured voltage at sensor 100 is above a certain $NO_2$ gas concentration. Plural gas concentrations, as shown in FIG. 23, are associated with plural voltages $V_{GS}$, that are applied to the transistor T1. Thus, each of the voltages $V_{GS}$ applied between the gate G and source S of the transistor T1, is associated with a corresponding $NO_2$ gas concentration, and thus, these voltages are sequentially applied to the sensor T1 after which the inverter generates a logical value 0 or 1. This process is illustrated in FIG. 24, where the top part of the figure illustrates the various voltages $V_{GS}$ that are sequentially applied to the sensor T1, the middle part of the figure illustrates the voltage $V_{inv}$ received by the inverter 2230 from the sensor 100 and transistor T1, and the lower part of the figure illustrates the logical values generated by the invertor 2230 as a result of the received voltages, i.e., the digital code corresponding to each measured gas concentration. In this specific example, the voltages $V_{GS}$ were selected to correspond to the gas concentrations of 0.5, 1, 2.5, 4, and 5 ppm. Those skilled in the art would understand that more or less voltages $V_{GS}$ and associated gas concentrations may be selected, and also that other gas concentrations may be selected with the desired voltages.

The system 2200 is configured in this embodiment to include the first transistor 100 having a gate G electrically connected to a drain D, a second transistor T1 having a gate G connected to a variable power source 2210, and the inverter 2230 being connected to a source S of the first transistor 100 and a drain D of the second transistor T1.

The system 2200 can in fact be operated in two modes. In a first simplified mode, it can be operated by applying a constant $V_{GS}$ voltage that can be tuned to detect a particular concentration of the $NO_2$ gas, such that the inverter 2230's output will be the logic high in the presence of the $NO_2$ gas (calibrated concentration). For the second mode, the system 2200 can be operated sequentially, to obtain a digital output like the flash mode discussed with regard to FIG. 17. Multiple $V_{GS}$ amplitudes are tuned to make the $V_{inv}$ reaches the threshold (input logic low of inverter) of the inverter to trigger a transition for various $NO_2$ concentrations. Passivated TFT T1 is continuously biased at one of the possible $V_{GS}$ voltages, and when there is $NO_2$ gas exposure, the inverter triggers a transition after a specific concentration is detected. To obtain the concentration output digitally, the $V_{GS}$ voltage (tuned voltages) is stepped and the corresponding output can be read. By reading the corresponding output, the $NO_2$ gas concentration can be quantified as illustrated in FIG. 23.

This second mode of operation of the system 2200 can be very power efficient and more compact, but at the cost of the speed in detection as each digit in the final code is generated in succession, one by one. A transient analysis that was carried out by exposing the system 2200 to various NO$_2$ gas concentrations (from 0.5 ppm to 5 ppm) and the response of this configuration is illustrated in FIG. 24. The V$_{GS}$ voltage for 5 different levels was calibrated to have an output logic high for five different concentrations of the NO$_2$ gas and the voltage was applied sequentially to the sensor after the exposure to the NO$_2$ gas. At each concentration, V$_{inv}$ (see FIG. 24) is shown corresponding to the applied V$_{GS}$ voltage. When V$_{inv}$ crosses the threshold voltage (1.8 V) for the input logic low, the output of the inverter makes a transition to the logic high ('1'). The digital output quantifying the NO$_2$ gas concentration for n=5 is shown in FIG. 24, bottom part, i.e., 11000 (for concentration >1 ppm). In this configuration, only one TFT sensor 100 and one passivated TFT transistor T1 are used as the n-levels of the voltage V$_{GS}$ are tuned to obtain the n-bit digital output.

Figure 25A:
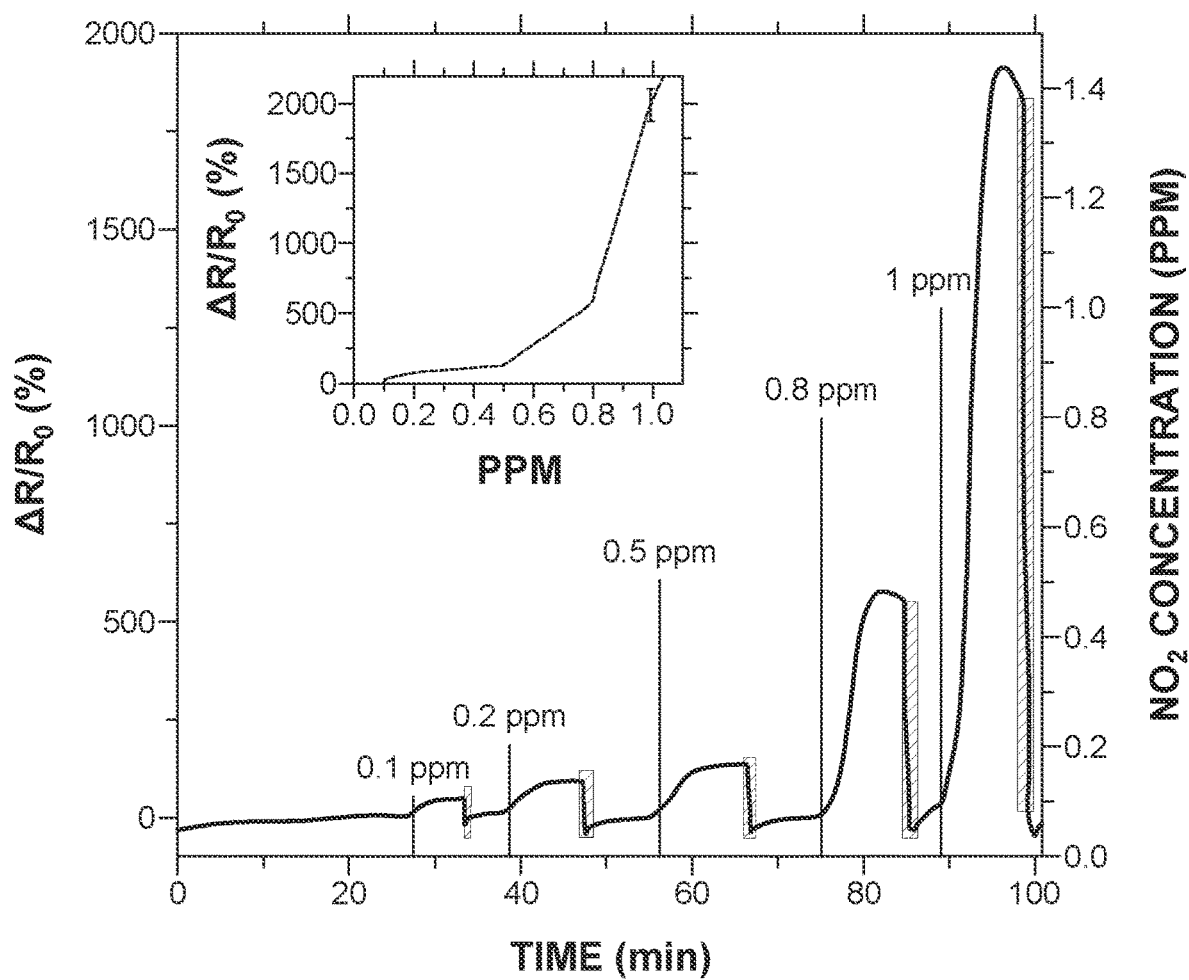
FIGS. 25A and 25B illustrate the response of the IGZO thin-film in the resistive mode after exposure to various concentrations of the gas.
Figure 25B:
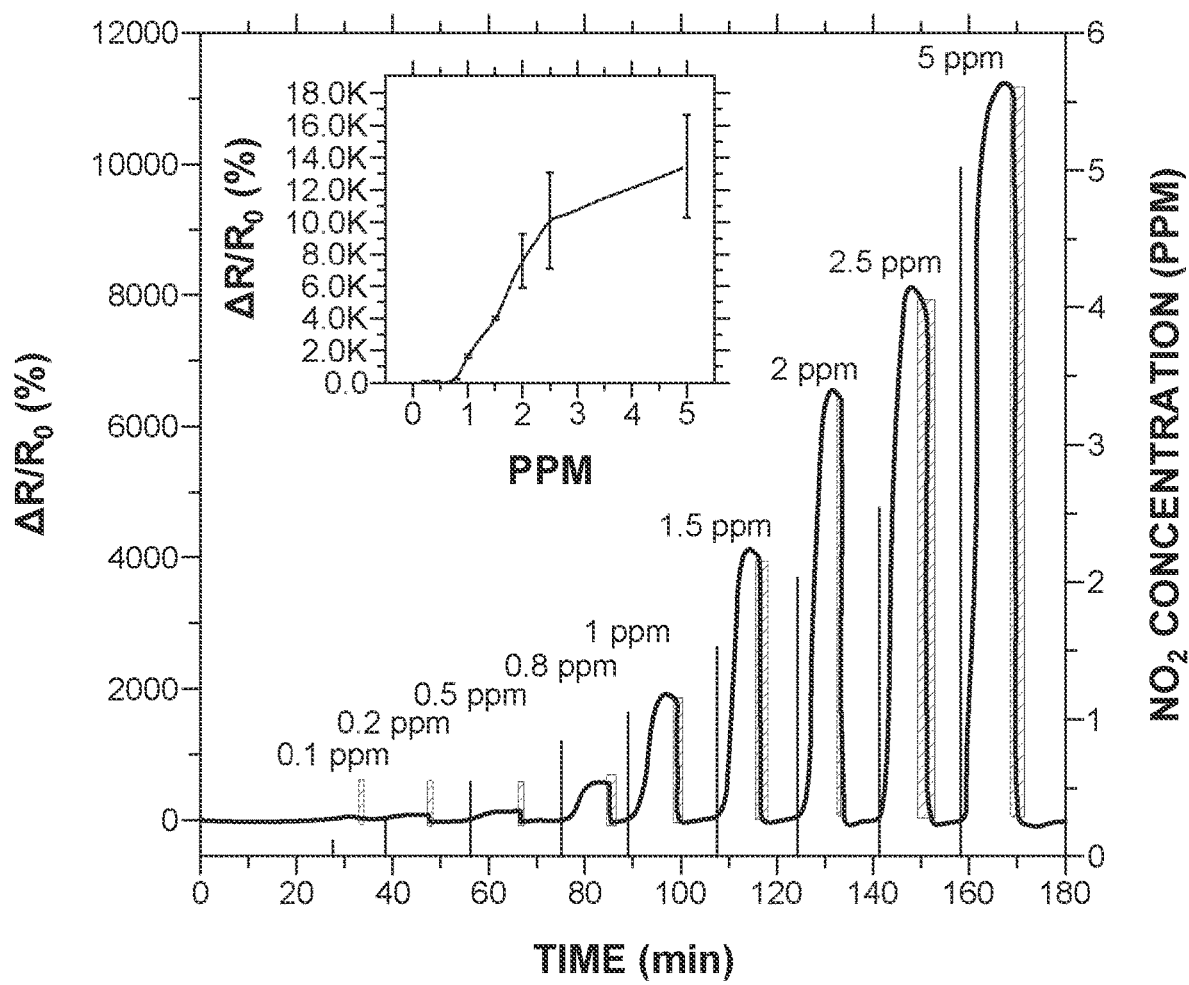

The performance of the IGZO sensor 100 as a chemi-resistor is now discussed. Apart from using the sensor 100 in the TFT mode, it can also be operated as a chemi-resistor. The baseline resistance of the semiconducting IGZO channel 106 is in the order of mega ohms due to the interdigitated electrode configuration, which allows the sensor 100 to be used as an IGZO based chemi-resistor. The top interdigitated electrodes 108A and 108B of the IGZO TFT sensor 100 are connected in this embodiment to the two terminals of an LCR meter while the gate 102 is floating, and the NO$_2$ gas response is evaluated by measuring the resistance vs time in the Cp-RP mode of the LCR meter at 10 kHz frequency and repeated transient analysis as previously discussed. A significant variation in the resistance is observed in this mode, as shown in FIGS. 25A and 25B, and the recovery of the device is achieved through the illumination by the blue LED after each exposure. The change in the resistance of the sensor 100 further confirms the change in the conductivity of the IGZO thin-film 106 due to the adsorption of the NO$_2$ gas. During the recovery period, the conductivity of the channel 106 improved by the photo generated carriers after illumination by the blue LED. The decrease in the conductivity of the channel 106 is exponential with the increase in the concentration of the NO$_2$ gas. This multi-transduction behavior of the IGZO TFT 106 allows the implementation of the sensor 100 as a NO$_2$ gas sensor either in the TFT mode discussed above with regard to the systems 1700 and 2200, or in the chemi-resistive mode. The TFT mode provides a linear response whereas the chemi-resistor mode provides an exponential response, as illustrated in the insert of FIG. 25A.

The above discussed embodiments provide various configurations of smart integrated sensory microsystems, and demonstrate a 3-bit digital output in the flash mode and a 5-bit digital output in the sequential mode. The digital output is in a thermometer code format proportional to the NO$_2$ gas concentration. The microsystems discussed with regard to the figures are sensing units without the traditional readout circuits, which means that they are inexpensive, compact and easily deployable in large scale for air quality monitoring. The common component of the above systems is the IGZO based gas sensor for the low concentration of the NO$_2$ gas detection. The specific composition of the IGZO thin-film discussed herein is the first report of a metal oxide TFT based gas sensor for room temperature sensing that uses light activation to regenerate the sensor. The IGZO thin-film is used as both an active layer for sensing the gas and also as a channel layer for the fabricated IGZO TFT sensor. The surface of the active IGZO layer is oxidized at room temperature due to the adsorption of the NO$_2$ gas, thereby significantly increasing the resistance of the channel, which results in the shift of V$_{th}$ and I$_D$. Thus, the IGZO based sensors show an excellent sensitivity of 12 nA/ppb and 15 mV/ppb for I$_D$ and V$_{th}$ respectively. Furthermore, the selectivity performance of these systems was investigated by comparing with different oxidizing and reducing gases. Two configurations were discussed herein, i.e., 3-bit and 5-bit gas concentrations to digital converters (GCDC) incorporating readout and ADC modules with the IGZO TFT as the basic element of the sensor. However, the embodiments discussed herein are applicable to any n-bit system. The limit of detection of the sensor was found to be as low as 100 ppb. The developed microsystems have the potential to be integrated with the Internet of Things (IoT) nodes for smart cities. Moreover, the developed sensor can also be used as a chemi-resistor for the NO$_2$ gas detection.

Figure 26:
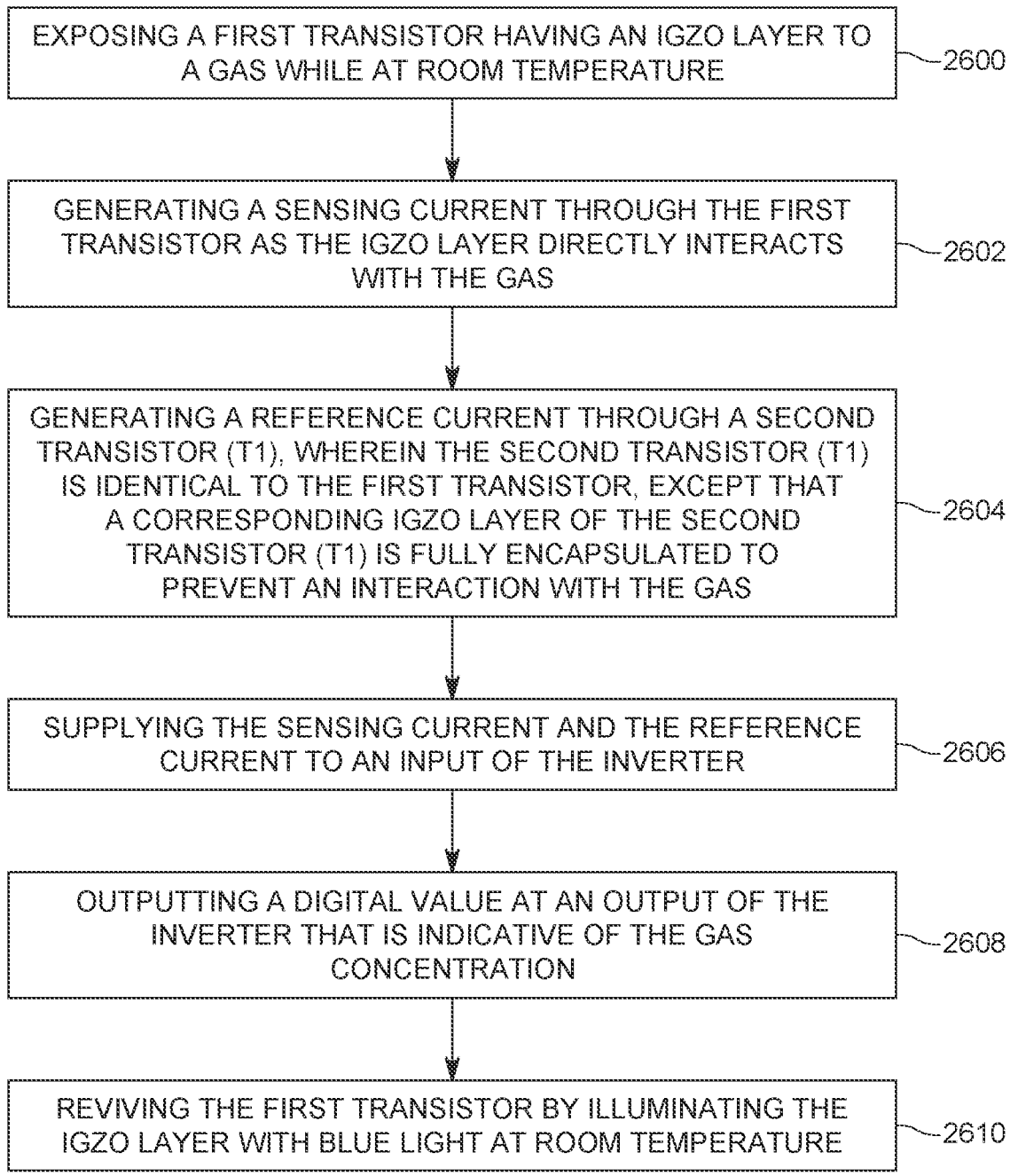
FIG. 26 is a flow chart of a method for measuring the concentration of a gas with a system having an IGZO based transistor.

FIG. 26 is a flow chart of a method for measuring a gas concentration with the IGZO based sensor 100. The method includes a step 2600 of exposing a first transistor 100 having an IGZO thin-film 106 to a gas while at room temperature, a step 2602 of generating a sensing current through the first transistor 100 as the IGZO active layer directly interacts with the gas, a step 2604 of generating a reference current through a second transistor (T1), wherein the second transistor (T1) is identical to the first transistor 100, except that a corresponding IGZO thin-film of the second transistor (T1) is fully encapsulated to prevent an interaction with the gas, a step 2606 of supplying the sensing current and the reference current to an input of the inverter 1730, 2230, a step 2608 of outputting a digital value at an output of the inverter that is indicative of the gas concentration, and a step 2610 of reviving the first transistor by illuminating the IGZO thin-film 106 with blue light at room temperature.

The disclosed embodiments provide an IGZO based sensor for detecting a gas concentration. In one embodiment, the sensor is integrated with a low power circuit for directly and digitally providing an output illustrative of the measured gas concentration. It should be understood that this description is not intended to limit the invention. On the contrary, the embodiments are intended to cover alternatives, modifications and equivalents, which are included in the spirit and scope of the invention as defined by the appended claims. Further, in the detailed description of the embodiments, numerous specific details are set forth in order to provide a comprehensive understanding of the claimed invention. However, one skilled in the art would understand that various embodiments may be practiced without such specific details.

Although the features and elements of the present embodiments are described in the embodiments in particular combinations, each feature or element can be used alone without the other features and elements of the embodiments or in various combinations with or without other features and elements disclosed herein.

This written description uses examples of the subject matter disclosed to enable any person skilled in the art to practice the same, including making and using any devices or systems and performing any incorporated methods. The patentable scope of the subject matter is defined by the claims, and may include other examples that occur to those skilled in the art. Such other examples are intended to be within the scope of the claims.

REFERENCES

[1] A. Dey, "Semiconductor metal oxide gas sensors: A review," *Materials Science and Engineering*: B, vol. 229, pp. 206-217, 2018.

[2] O. Casals et al., "A Parts Per Billion (ppb) Sensor for $NO_2$ with Microwatt (muW) Power Requirements Based on Micro Light Plates," *ACS Sens*, vol. 4, no. 4, pp. 822-826, Apr. 26, 2019.

[3] K. Nomura, H. Ohta, A. Takagi, T. Kamiya, M. Hirano, and H. Hosono, "Room-temperature fabrication of transparent flexible thin-film transistors using amorphous oxide semiconductors," *Nature*, vol. 432, no. 7016, pp. 488-492, 2004/11/01 2004.

[4] K. S. Kim, C. H. Ahn, S. H. Jung, S. W. Cho, and H. K. Cho, "Toward Adequate Operation of Amorphous Oxide Thin-Film Transistors for Low-Concentration Gas Detection," *ACS Appl Mater Interfaces*, vol. 10, no. 12, pp. 10185-10193, Mar. 28, 2018.

[5] S. Knobelspies et al., "Photo-Induced Room-Temperature Gas Sensing with a-IGZO Based Thin-Film Transistors Fabricated on Flexible Plastic Foil," *Sensors (Basel)*, vol. 18, no. 2, Jan. 26, 2018.

[6] M.-J. Park, H.-S. Jeong, H.-J. Joo, H.-Y. Jeong, S.-H. Song, and H.-I. Kwon, "Improvement of $NO_2$ gas-sensing properties in InGaZnO thin-film transistors by a pre-biasing measurement method," *Semiconductor Science and Technology*, vol. 34, no. 6, 2019.

[7] Y. Kang, H. Song, H. H. Nahm, S. H. Jeon, Y. Cho, and S. Han, "Intrinsic nature of visible-light absorption in amorphous semiconducting oxides," *APL Materials*, Article vol. 2, no. 3, 2014, Art. no. 032108.

[8] N. Vorobyeva et al., "Highly Sensitive ZnO(Ga, In) for Sub-ppm Level NO2 Detection: Effect of Indium Content," *Chemosensors*, vol. 5, no. 2, 2017.

What is claimed is:

1. A gas sensor comprising:
a gate electrode;
a dielectric layer covering one surface of the gate electrode;
an indium (In) gallium (Ga) zinc (Zn) oxide (O) (IGZO) thin-film formed over the dielectric layer, and
first and second metallic electrodes formed on a surface of the IGZO thin-film to act as source and drain, respectively,
wherein the IGZO thin-film has an In mass concentration of 11%+/−3%, Ga mass concentration of 11%+/−3%, Zn mass concentration of 7%+/−3%, and O mass concentration of 71%+/−3%, with a sum of the mass concentrations being 100%, and
wherein the gas interacts with the IGZO thin-film and changes a current through the IGZO thin-film.

2. The sensor of claim 1, wherein the In mass concentration is 11%, the Ga mass concentration is 11%, the Zn mass concentration is 7%, and the O mass concentration is 71%.

3. The sensor of claim 1, wherein a thickness of the IGZO thin-film is between 5 and 20 nm.

4. The sensor of claim 3, wherein the gate electrode is made of Si, the dielectric layer is made of $SiO_2$, the IGZO thin-film includes no other materials, and the first and second electrodes are formed directly on the IGZO thin-film.

5. A gas detection system for determining a concentration of a gas, the system comprising:
a first transistor having an indium (In) gallium (Ga) zinc (Zn) oxide (O) (IGZO) thin-film formed over a dielectric layer, wherein the IGZO thin-film interacts with the gas and changes a sensing current through the first transistor;
a second transistor (T1) electrically connected to the first transistor to form a master branch, wherein the second transistor (T1) has an identical structure as the first transistor, and a corresponding IGZO thin-film is encapsulated with a material to prevent an interaction between the IGZO thin-film of the second transistor (T1) and the gas, while the IGZO thin-film of the first transistor is free to directly interact with the gas;
third and fourth transistors (T2, T3) electrically connected to each other and forming a secondary branch, wherein the third and fourth transistors (T2, T3) are identical to the second transistor (T1); and
an inverter electrically connected to the third and fourth transistors (T2, T3),
wherein the inverter receives a voltage due to (1) a reference current from the third transistor (T2), and (2) a current from the fourth transistor (T3), which is identical to the sensing current of the first transistor, and outputs a digital value indicative of the concentration of the gas.

6. The system of claim 5, wherein a supply voltage $V_{DD1}$ to the third transistor is selected to correspond to a given concentration of the gas so that if the concentration of the gas is below the given concentration, the inverter generates a 0 value, and if the concentration of the gas is above the given concentration, the inverter generates a 1 value.

7. The system of claim 5, wherein no analog to digital circuitry is used to generate the digital value indicative of the concentration of the gas.

8. The system of claim 5, wherein the first transistor comprises:
a gate electrode;
the dielectric layer covering one surface of the gate electrode;
the IGZO thin-film formed over the dielectric layer, and
first and second metallic electrodes formed on a surface of the IGZO thin-film to act as source and drain, respectively,
wherein the IGZO thin-film has an In mass concentration of 11%+/−3%, Ga mass concentration of 11%+/−3%, Zn mass concentration of 7%+/−3%, and O mass concentration of 71%+/−3% with a total sum of the mass concentrations being 100%.

9. The system of claim 5, wherein a gate of the second transistor (T1) is directly connected to a gate of the fourth transistor (T3), and a drain of the first transistor is directly connected to the gate of the first transistor.

10. The system of claim 9, wherein a source of the first transistor is directly connected to the gates of the second and fourth transistors.

11. The system of claim 5, further comprising:
an additional secondary branch having fifth and sixth transistors identical to the second transistor and the additional secondary branch is configured identical to the secondary branch; and an additional inverter electrically connected to the fifth and sixth transistors.

12. The system of claim 11, wherein a supply voltage $V_{DD1}$ to the third transistor is selected to correspond to a first given concentration of the gas, and a supply voltage $V_{DD2}$ to the fifth transistor is selected to correspond to a second given concentration of the gas, which is larger than the first given concentration, so that (a) when the concentration of the gas is below the first given concentration, the inverter generates a 0 value and the additional inverter generates a 0 value, (b) when the concentration of the gas is above the first given concentration but below the second given concentration, the inverter generates a 1 value and the additional inverter generates a 0 value, and (c) when the concentration of the gas is above the second given concentration, the inverter generates a 1 value and the additional inverter generates a 1 value.

13. The system of claim 11, wherein the secondary branch and the additional secondary branch have the same supply voltage, and dimensions of the third and fourth transistors are different from dimensions of the fourth and fifth transistors.

14. A gas detection system for determining a concentration of a gas, the system comprising:
   a first transistor having a gate electrically connected to a drain;
   a second transistor (T1) having a gate connected to a variable power source; and
   an inverter connected to a source of the first transistor and to a drain of the second transistor (T1),
   wherein the first transistor includes an indium (In) gallium (Ga) zinc (Zn) oxide (O) (IGZO) thin-film, which is exposed to an ambient,
   wherein the second transistor includes a corresponding IGZO thin-film, which is encapsulated to not be exposed to the ambient, and
   wherein for each applied voltage $V_{GS}$ at the gate of the second transistor T1, the inverter receives a voltage due to a sensing current generated by the first transistor and a reference current generated by the second transistor, and generates a digital value indicative of the concentration of the gas.

15. The system of claim 14, wherein plural, discrete, voltages $V_{GS}$ are applied successively at the gate of the second transistor T1 to successively generate corresponding digital values associated with the concentration of the gas.

16. The system of claim 14, wherein the first transistor comprises:
   a gate electrode;
   the dielectric layer covering one surface of the gate electrode;
   the IGZO thin-film formed over the dielectric layer, and
   first and second metallic electrodes formed on a surface of the IGZO thin-film to act as source and drain, respectively,
   wherein the IGZO thin-film has an In mass concentration of 11%+/−3%, Ga mass concentration of 11%+/−3%, Zn mass concentration of 7%+/−3%, and O mass concentration of 71%+/−3% with a total sum of the mass concentrations being 100%.

17. The system of claim 14, wherein the inverter has a given threshold voltage, and the sensing current and the reference current applied to the inverter determine an inverter voltage, and when the sensing current is less than the reference current, an output digital value is 1, and 0 otherwise.

18. The system of claim 17, wherein each applied voltage $V_{GS}$ generates a corresponding 1 or 0 value so that a final output of the inverter includes a sequence of 1s and 0s, and a number of the digits in the sequence are equal to the number of applied voltages $V_{GS}$.

19. The system of claim 18, wherein each sequence of 1s and 0s corresponds to a given gas concentration range.

* * * * *